United States Patent
Burstein et al.

(10) Patent No.: US 12,171,558 B2
(45) Date of Patent: Dec. 24, 2024

(54) SYSTEM AND METHOD FOR SCREENING CONDITIONS OF DEVELOPMENTAL IMPAIRMENTS

(71) Applicant: KNOWME SOLUTIONS LTD., Bnei Zion (IL)

(72) Inventors: Anat Burstein, Bnei Zion (IL); Avraham Peretz, Beer Yaacov (IL)

(73) Assignee: KNOWME SOLUTIONS LTD., Bnei Zion (IL)

( * ) Notice: Subject to any disclaimer, the term of this patent is extended or adjusted under 35 U.S.C. 154(b) by 551 days.

(21) Appl. No.: 17/437,856

(22) PCT Filed: Mar. 9, 2020

(86) PCT No.: PCT/IL2020/050276
§ 371 (c)(1),
(2) Date: Sep. 10, 2021

(87) PCT Pub. No.: WO2020/183460
PCT Pub. Date: Sep. 17, 2020

(65) Prior Publication Data
US 2022/0142535 A1 May 12, 2022

Related U.S. Application Data

(60) Provisional application No. 62/816,234, filed on Mar. 11, 2019.

(51) Int. Cl.
*A61B 5/16* (2006.01)
*A61B 5/00* (2006.01)
(Continued)

(52) U.S. Cl.
CPC ............ *A61B 5/16* (2013.01); *A61B 5/02055* (2013.01); *A61B 5/4803* (2013.01);
(Continued)

(58) Field of Classification Search
CPC ....................................................... A61B 5/16
(Continued)

(56) References Cited

U.S. PATENT DOCUMENTS

2015/0099946 A1* 4/2015 Sahin ................. A61B 7/04
600/301
2017/0069216 A1 3/2017 Vaughan et al.
(Continued)

OTHER PUBLICATIONS

International Search Report for Application No. PCT/IL2020/050276, mailed on May 27, 2020.

*Primary Examiner* — Nadia A Mahmood
(74) *Attorney, Agent, or Firm* — PEARL COHEN ZEDEK LATZER BARATZ LLP

(57) ABSTRACT

A system and a method of performing screening tests for diagnosing a developmental condition of a human subject may include: receiving one or more profile data elements pertaining to the human subject; receiving one or more first behavioral data elements that may include information that is indicative of a behavior of a human subject from one or more data sources; analyzing the one or more first behavioral data elements in view of the one or more profile data elements to obtain a suspected impediment of development of the human subject; and presenting to the human subject a personalized test, adapted to diagnose the developmental condition of the human subject in view of the suspected impediment, to perform on a UI of a computing device according to the suspected impediment.

18 Claims, 6 Drawing Sheets

(51) Int. Cl.
  *A61B 5/0205* (2006.01)
  *G16H 10/60* (2018.01)
  *G16H 20/70* (2018.01)
  *G16H 50/20* (2018.01)
  *G16H 50/70* (2018.01)

(52) U.S. Cl.
  CPC ........... *A61B 5/7435* (2013.01); *G16H 10/60* (2018.01); *G16H 20/70* (2018.01); *G16H 50/20* (2018.01); *G16H 50/70* (2018.01)

(58) Field of Classification Search
  USPC ....................................................... 600/301
  See application file for complete search history.

(56) References Cited

U.S. PATENT DOCUMENTS

| | | |
|---|---|---|
| 2017/0364636 A1 | 12/2017 | Chen |
| 2018/0070823 A1 | 3/2018 | Blackwell et al. |
| 2019/0019581 A1 | 1/2019 | Vaughan et al. |

\* cited by examiner

SYSTEM AND METHOD FOR SCREENING CONDITIONS OF DEVELOPMENTAL IMPAIRMENTS

CROSS-REFERENCE TO RELATED APPLICATIONS

This application is a National Phase Application of PCT International Application No. PCT/IL2020/050276, International Filing Date Mar. 9, 2020, claiming the benefit of U.S. Provisional Patent Application No. 62/816,234, filed Mar. 11, 2019, which is hereby incorporated by reference.

FIELD OF THE INVENTION

The present invention relates generally to the field of healthcare. More specifically, the present invention relates to the field of screening tools for diagnosing a developmental condition of a human subject.

BACKGROUND OF THE INVENTION

Developmental delays may be difficult to diagnose, whereas an early detection of such delays may be crucial to an individual's well-being, advancement and quality of life. Traditional diagnosis and treatment plans for people with disability involve diagnostic processes that may consume time and money. Additionally, diagnostic processes of developmental impediments and developmental delays are often long and emotionally stressful, and may rely on indirect measurements based on observations and questionnaires that may be conducted outside the human subject's natural environment, e.g., at a time and/or location that may be unnatural or inconvenient to the human subject.

This negatively affects over one billion people (15% of the world's population) with disabilities who, according to the World Report on Disability, have difficulty accessing appropriate health, rehabilitation, support, education, and employment opportunities.

Disabled people may face obstacles and barriers when accessing therapeutic services. Such barriers may include prohibitive costs; affordability of health services and transportation; limited availability of local services or lack of appropriate services; physical barriers; inadequate skills and knowledge of health workers; mistreatment, abuse, exploitation or denial of care.

Some of the most discriminating barriers are programmatic & geographical barriers that limit the effective delivery of a public health or healthcare program for people with different types of impairments. Examples of programmatic barriers include: inconvenient scheduling; lack of accessible equipment; insufficient time set aside for medical examination and procedures; little or no communication with patients or participants; and care providers' attitude, knowledge of the array or variety of developmental impediments, lack of ability to asses human development in the human subject's natural environment at times most appropriate according to the subject's biological clock, and understanding of people with disabilities.

According to the United Nations International Children's Emergency Fund (UNICEF), children with disabilities are one of the most marginalized and excluded groups in society. Facing daily discrimination in the form of negative attitude and lack of adequate policy and legislation, they are effectively barred from realizing their rights to healthcare, education, and even survival. Estimates suggest that there are at least 93 million children with disabilities in the world, but numbers could be much higher. Disabled children are often included among the poorest members of the population: They are less likely to attend school, access medical services, or have their voices heard in society. Their disabilities also place them at a higher risk of physical abuse, and often exclude them from receiving proper nutrition or humanitarian assistance in emergencies.

The World health organization (WHO) together with UNICEF produced a discussion paper that describes the importance of ensuring access to interventions which can help people with disability, and especially young children, reach their full potential. The paper acknowledges early childhood is a crucial phase of growth and development as experiences during this time influence outcomes across the entire course of an individual's life. For all mankind, early childhood provides an important window of opportunity to prepare the foundation for life-long learning and participation, while preventing potential delays in development and disabilities. For children who experience disability, it is a vital time to ensure access to interventions which can help them reach their full potential. WHO and UNICEF acknowledge that in the perspective of society, early intervention is crucial to promote methods to ensure that all children achieve their full and effective participation in society, on an equal basis with others (Convention on the Rights of Persons with Disabilities, Article 1).

The Center on the Developing Child at Harvard University summarized the actualities crucial for understanding the importance of early childhood to the learning, behavior, and health of later life and explain why addressing challenges as soon as possible is easier and more effective than trying to fix them later. In the first few years of life, more than 1 million new neural connections are formed every second through the interaction of genes and a baby's environment and experiences, especially "serve and return" interaction with adults, or what developmental researchers call contingent reciprocity. These are the connections that build brain architecture—the foundation upon which all later learning, behavior, and health depend.

Unfortunately, children with disabilities and their families are confronted by barriers including inadequate legislation and policies, negative attitudes, inadequate services, and lack of accessible environments that deny or delay prompt adequate supports required to meet their rights and needs. If children with developmental delays or disabilities and their families are not provided with timely and appropriate early intervention, support and protection, their difficulties can become more severe—often leading to lifetime consequences, increased poverty and profound exclusion. The UN Convention on the Rights of the Child (CRC) and the Convention on the Rights of Persons with Disabilities (CRPD) highlight how children with disabilities have the same rights as other children—for example to health care and insurance, nutrition, education, social inclusion and protection from violence, abuse and neglect. Ensuring access to appropriate support, such as early childhood intervention (ECI) and education, can fulfil the rights of children with disabilities, promoting rich and fulfilling childhoods and preparing them for full and meaningful participation in adulthood.

In order to attain appropriate interventions as soon as possible, the importance of early screening is crucial for the child to receive the services and interventions they need to thrive and maximize their potential.

To date, validated developmental screening tools used by physicians that may assess whether children require further clinical investigation include parent-completed (based on the parent's report alone) questioners and directly administered checklist based on direct physician and health practitioners' observation of the child. Directly administered tools are more comprehensive, but take longer to complete. They are best used as follow-up to an abnormal initial parent-completed screening test, and are typically conducted at a subspecialty consultation. (K. Vitrikas, MD. D. Savard MD, M. Bucaj DO, American Family Physician. 2017 Jul. 1; 96(1):36-43). Essential components of the screening process include attention to parental concerns and observations, examination of explicit developmental achievements and observation of parent-child interaction. In March 2020 a comprehensive study regarding trends in pediatricians' developmental screening: 2002-2016, published in Pediatrics—the official journal of the American Academy of Pediatrics (AAP) showed that only 23% of pediatricians in 2002 reported using a standardized developmental screening tool, citing lack of time, staff, and reimbursement as barriers. In order to improve screening rates, AAP released guidelines calling for developmental surveillance at every visit and use of a standardized screening tool at the 9-, 18-, and 24- or 30-month well-child visits advancing the reported rate of standardized screening tool to nearly 63% but with significant geographic variation. This represents a tripling in screening over 15 years and a doubling since the 2006 guidelines. The AAP issue of guidelines for pediatricians to improve the early identification of children with developmental disorders through surveillance and screening displays AAP's ongoing educational efforts to promote screening in light of the basic understanding the crucial importance of early detection and intervention. To further increase the rates of both developmental screening and referral of patients with concerns for treatment, increased attention should be focused on improving screening towards early detection. (Paul H. Lipkin, Michelle M. Macias, Briella Baer Chen, Daniel Coury, Elizabeth A. Gottschlich, Susan L. Hyman, Blake Sisk, Audrey Wolfe and Susan E. Levy, Pediatrics, March 2020)

Studies point to the currently low rates of detection of developmental delays approximately 15% of children are estimated to have developmental disorders, only 30% of children with developmental delays are diagnosed before school entrance. Low-income children are at greater risk for developmental delays, with increased rates of developmental delays reported in lower income children compared to higher income children. More specifically, single-parent households and households in poverty have an increased rate of children with developmental problems. Additionally, children with public health insurance are more likely to have special health care needs including developmental delays, and are at increased risk for long-term disability compared to children of higher socioeconomic status.

These statistics show that to date, improving detection rates while speeding up detection processes are crucial. Technology can disrupt this slow un-efficient process which requires time, money and emotional resources from all stakeholders—people with disabilities, families, caregivers, health professionals, health systems, insurance companies, educational frameworks and cities infrastructures, while efficiently advancing periodic screening and ongoing assessment, documentation process, medical record, making sure that under-identify young children with developmental delays will be a story of the past and mass data for enhancing interventions and research increase.

The World Bank studies show that evidence from both developed and developing countries suggests a potential return rate of 7-16 percent annually from high-quality early childhood programs targeting vulnerable groups. Returns are also linked to a range of positive impacts in education and health, reduced risky behaviors and increased productivity among adults alongside lessening hardship and suffering for children, families and communities.

SUMMARY OF THE INVENTION

Accurate diagnosis of a developmental condition, including identification of a source of a developmental delay or impediment may enable tailoring a treatment plan to meet an individual's needs. For example, a child diagnosed with autism will need very different care than a child with Down syndrome, even though they may both struggle with language and communication capabilities Embodiments of the invention may improve screening and diagnosis of developmental impediments, and may allow dissemination of treatment of the diagnosed developmental condition.

Embodiments of the invention may provide digital empowerment for people with disabilities and their families by an accessible, easy to use screening tool that may match best practices for treatment and enabling this vulnerable population to maximize their developmental potential.

Moreover, smart device based diagnostic platforms may offer real-time access, analytics and collaboration with specialists and stakeholders in any location. The term "smart device" may refer herein to any electronic computing device as elaborated herein (e.g., in relation to element 1 of FIG. 1), including for example a smartphone, a tablet computer, a smart watch, and the like.

Embodiments of the invention may include a method and a system that may automatically and adaptively assess a developmental condition of a human subject, screen conditions in which a suspected impediment to typical or normal development exists and suggest a method of treatment and a report or roadmap for development.

Embodiments of the invention may include a method and a system that may perform screening tests for diagnosing a developmental condition of a human subject.

Embodiments may include: receiving one or more profile data elements pertaining to the human subject; receiving one or more first behavioral data elements that may include information that may be indicative of a behavior of a human subject from one or more data sources; analyzing the one or more first behavioral data elements in view of the one or more profile data elements to obtain a suspected impediment of development of the human subject; and presenting to the human subject a personalized test, adapted to diagnose the developmental condition of the human subject in view of the suspected impediment, to perform on a user interface (UI) of a computing device according to the suspected impediment.

According to some embodiments, analyzing the one or more first behavioral data elements may include: providing at least one of the one or more first behavioral data elements and the one or more profile data elements as input to a first classifier; obtaining from the first classifier an indication of the suspected impediment of development of the human subject.

According to some embodiments, the test may be personalized according to at least one of: a profile data element; a data element corresponding to an environmental condition at the human subject's environment; a data element corresponding to a physical condition of the human subject; a data element corresponding to a medical record of the human subject; and a data element corresponding to a structured input of the human subject.

According to some embodiments, presenting the personalized test to perform on the UI may include: presenting the personalized test by an application on the UI of the computing device; receiving one or more second behavioral data elements that may include information that may be indicative of a behavior of the human subject from the computing device;

providing, as input to a second classifier, at least one of: the one or more first behavioral data elements, the one or more second behavioral data elements, the one or more profile data elements, and the indication of the suspected impediment; and obtaining from the second classifier a diagnosis of developmental condition of the human subject.

According to some embodiments, diagnosis of developmental condition may include one or more of: the suspected impediment; a developmental condition classification of the human subject corresponding to suspected impediment; a level of diagnosis certainty; and an indication of one or more behavioral data elements that may correspond to the suspected developmental impediment.

Embodiments may include producing at least one recommended roadmap for treatment based on at least one of the diagnosis of developmental condition and the one or more profile data elements.

Embodiments may include producing at least one of: a predicted roadmap of a developmental condition of the human subject; and a predicted roadmap of behavior of the human subject, based on at least one of the diagnosis of developmental condition and the one or more profile data elements.

According to some embodiments, the one or more data sources may be selected from a list including: a structured text document; a medical database; and at least one sensor adapted to sense a physical property indicative of a behavior of the human subject.

According to some embodiments, the sensor may be a wearable sensor, adapted to sense at least one physical property and wherein the physical property may be selected from a list that may include one or more of: skin temperature, skin moisture, skin pH, skin conductivity, pulse rate, blood pressure, movement, acceleration, firmness of touch, brain wave signals, and a spectral distribution of skin color.

The sensor may be included within a computing device, adapted to execute at least one application, and the application may be adapted to obtain from the sensor at least one behavioral data element that may include information that may be indicative of a behavior of the human subject.

The application may be selected from a list that may include: a spontaneous, interactive application; a spontaneous, non-interactive application; and a non-spontaneous, interactive application.

According to some embodiments, at least one behavioral data element may be a voice of the human. The application may be configured to record a voice of the human subject during presentation of the application on the UI and analyze the recorded voice to obtain a value of at least one acoustic and/or frequency parameter or feature that may be indicative of at least one of a behavior and a developmental condition of the human subject.

Alternatively, or additionally, the application may be configured to record the voice of the human subject during a normal operation of the computing device by the human subject and analyze the recorded voice to obtain a value of at least one acoustic parameter that may be indicative of at least one of a behavior and a developmental condition of the human subject.

According to some embodiments, at least one behavioral data element may be a picture and/or a video of the human subject. The application may be configured to take at least one picture of the human subject during presentation of the application on the UI and analyze the at least one picture to obtain a value of at least one visual parameter or feature that may be indicative of at least one of a behavior and a developmental condition of the human subject.

Alternatively, or additionally, the application may be configured to take at least one picture of the human subject during a normal operation of the computing device by the human subject and analyze the at least one picture to obtain at least one visual parameter or feature that may be indicative of at least one of a behavior and a developmental condition of the human subject.

According to some embodiments, at least one behavioral data element may be a movement of the human subject. The application may be configured to monitor at least one movement of the human subject during presentation of the application on the UI and analyze the at least one movement to obtain a value of at least one movement parameter and/or feature that may be indicative of at least one of a behavior and a developmental condition of the human subject.

Alternatively, or additionally, the application may be configured to monitor at least one movement of the human subject during a normal operation of the computing device by the human subject and analyze the at least one movement to obtain a value of at least one movement parameter and/or feature that may be indicative of at least one of a behavior and a developmental condition of the human subject.

Embodiments of the invention may include a system for performing screening tests for diagnosing a developmental condition of a human subject. Embodiments may include: a non-transitory memory device, wherein modules of instruction code are stored, and a processor associated with the memory device, and configured to execute the modules of instruction code. Upon execution of the modules of instruction code, the processor may be configured to perform at least one of: receive one or more profile data elements pertaining to the human subject; receive one or more first behavioral data elements that may include information that may be indicative of a behavior of a human subject from one or more data sources; analyze the one or more first behavioral data elements in view of the one or more profile data elements to obtain a suspected impediment of development of the human subject; and present to the human subject a personalized test, adapted to diagnose the developmental condition of the human subject in view of the suspected impediment, to perform on a UI of a computing device according to the suspected impediment.

Embodiments of the invention may include a method of performing screening tests for diagnosing a developmental condition of a human subject by at least one processor. Embodiments may include: obtaining one or more behavioral data elements that may include information indicative of a behavior of a human subject, during spontaneous, non-interactive utilization of a smart device (e.g., a smartphone, a tablet computer, etc.); analyzing the one or more behavioral data elements to obtain a suspected impediment of development of the human subject; and presenting to the human subject, on a user interface, a personalized test, adapted to diagnose the developmental condition of the human subject in view of the suspected impediment.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

Figure 1:
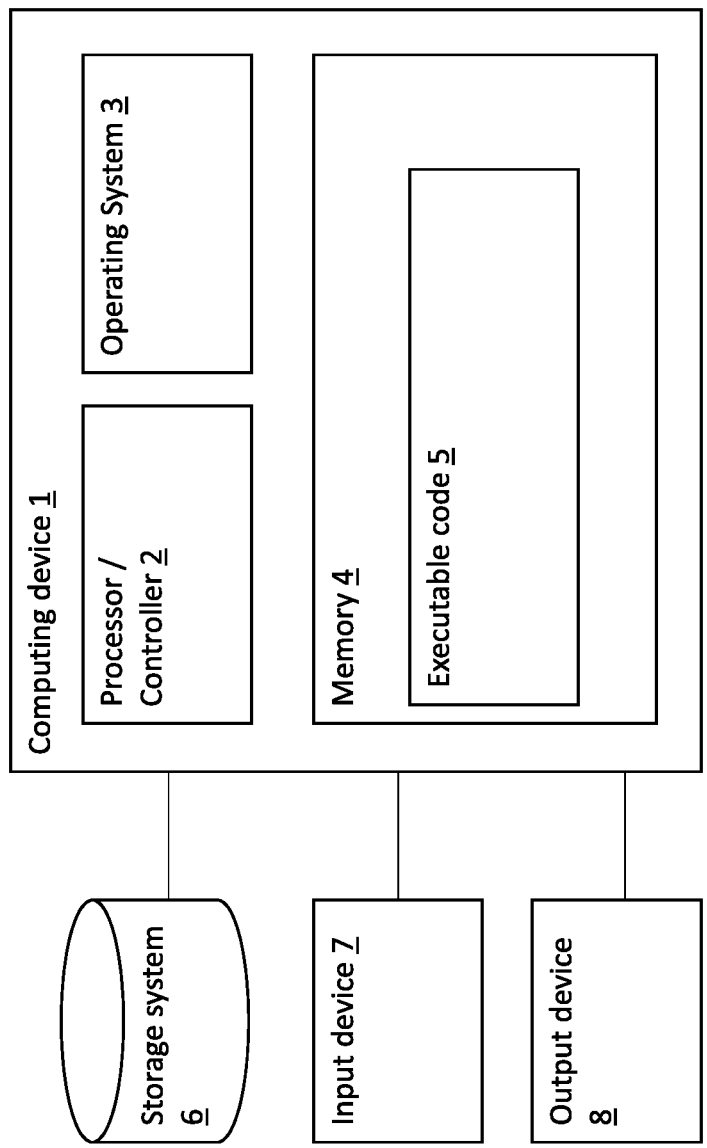
FIG. 1 is a block diagram, depicting a computing device which may be included in a system for adaptively performing personalized screening tests for diagnosing a developmental condition of the human subject, according to some embodiments.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention. Some features or elements described with respect to one embodiment may be combined with features or elements described with respect to other embodiments. For the sake of clarity, discussion of same or similar features or elements may not be repeated.

Although embodiments of the invention are not limited in this regard, discussions utilizing terms such as, for example, "processing," "computing," "calculating," "determining," "establishing", "analyzing", "checking", "synchronizing" or the like, may refer to operation(s) and/or process(es) of a computer, a computing platform, a computing system, or other electronic computing device (e.g., a wearable electronic computing device), that manipulates and/or transforms data represented as physical (e.g., electronic) quantities within the computer's registers and/or memories into other data similarly represented as physical quantities within the computer's registers and/or memories or other information non-transitory storage medium that may store instructions to perform operations and/or processes. Although embodiments of the invention are not limited in this regard, the terms "plurality" and "a plurality" as used herein may include, for example, "multiple" or "two or more". The terms "plurality" or "a plurality" may be used throughout the specification to describe two or more components, devices, elements, units, parameters, or the like. The term set when used herein may include one or more items. Unless explicitly stated, the method embodiments described herein are not constrained to a particular order or sequence. Additionally, some of the described method embodiments or elements thereof can occur or be performed simultaneously, at the same point in time, or concurrently.

Embodiments of the present invention include a method and a system for assessing a human subject's behavior, adaptively performing personalized screening tests for determining or diagnosing a developmental condition of the human subject, detecting a condition of impeded behavior and/or development, and/or producing a suggested roadmap for treatment, according to some embodiments.

As explained herein, the screening tests may be performed adaptively and be made personalized to a specific human subject in a sense that: (a) the tests may take into consideration at least one profile parameter of the human subject (e.g., the subject's age), and include a comparison with a typical or normally expected development of a human subject of a similar profile; (b) the tests may be performed hierarchically, over a number of stages, where each stage may be based on the outcome of the predecessor stage and may fine-tune the diagnosis or provide a sub classification of the human subject's developmental condition and/or developmental impediment; and (c) the tests may be performed sequentially through a long period of time, where each test may serve as a reference or a point for comparison with a previous developmental condition of the human subject.

The following table may serve as a reference to terms that are used herein.

TABLE 1

| | |
|---|---|
| Human subject | The term 'human subject' (HS) may be used herein to refer to a person (e.g., a child) upon whom embodiments of the present invention may perform one or more tests to assess their developmental condition. |
| Dev. condition | The term 'developmental condition' (DC) may be used herein to refer to a syndrome, diagnosable disease, condition or state of a HS's cognitive, mental, intellectual, emotional, physical or social condition. Embodiments of the present invention may apply one or more tests on the HS, monitor their behavior during the test, and assess the HS's DC in view of a personal profile of the user and in comparison, to an expected DC of a person having a similar profile. |
| Expected developmental condition | The term 'expected developmental condition' (EDC) may be used herein to refer to a typical or normal condition or state of a HS's cognitive, mental, intellectual, physical or social and/or developmental condition, in view of a respective profile, as elaborated herein. |

TABLE 1-continued

| | |
|---|---|
| Profile | The terms 'profile' or 'personal profile' may be used herein interchangeably to refer to one or profile parameters that may affect a HS's behavior and/or DC. Profile parameters may include for example, the HS's age, gender, a grade which the HS attends, a social background or condition, such as a school and/or another social environment which the HS attends, information pertaining to social relations, such as the quantity and quality of social ties and friends, ethnicity, financial status, geographic location and the like. |
| Dev. impediment | The term 'developmental impediment' may be used herein to refer to a physical, intellectual, emotional, mental or social cause or obstruction that may cause a delay or a barrier in a HS's development in relation to the expected DC. |
| Behavior | The term 'behavior' may be used herein to refer to one or more actions that may be, or may not be performed by a user, and may be monitored by an embodiment of the invention during the performance of a screening test. |
| Expected Behavior | The term 'expected behavior' (EB) may be used herein to refer to a typical or normal behavior of a HS during the performance of a screening test, in view of a respective profile, as elaborated herein. |
| Test, Screening test, screening tool | The terms 'test', 'screening test' and 'screening tool' may be used interchangeably to refer to any type of test or examination that may be performed by an embodiment of the present invention and may be adapted to provide an assessment of a DC and/or detect or diagnose a suspected developmental impediment of one or more HSs. The screening test may be performed hierarchically, sequentially or iteratively where each test may be adapted according to or take input from the outcome of a previous test, to fine-tune a diagnosis of the HS's DC. Embodiments of the invention may include a software application that may perform a test in at least one of a non-spontaneous, interactive form, a spontaneous, non-interactive form and a spontaneous, interactive form, as elaborated herein. |
| Neural network | The term 'neural network', e.g. a neural network implementing machine learning, may refer to an information processing paradigm that may include nodes, referred to as neurons, organized into layers, with links between the neurons. The links may transfer signals between neurons and may be associated with weights. A NN may be configured or trained for a specific task, e.g., pattern recognition or classification. Training a NN for the specific task may involve adjusting these weights based on examples. Each neuron of an intermediate or last layer may receive an input signal, e.g., a weighted sum of output signals from other neurons, and may process the input signal using a linear or nonlinear function (e.g., an activation function). The results of the input and intermediate layers may be transferred to other neurons and the results of the output layer may be provided as the output of the NN. Typically, the neurons and links within a NN are represented by mathematical constructs, such as activation functions and matrices of data elements and weights. A processor, e.g. CPUs or graphics processing units (GPUs), or a dedicated hardware device may perform the relevant calculations. |

Reference is now made to FIG. 1, depicting a computing device which may be included in a system for assessing a HS's behavior, adaptively performing personalized screening tests for diagnosing a DC of the HS and detecting a condition of impeded behavior and/or development, according to some embodiments.

Computing device 1 may include a processor or controller 2 that may be, for example, a central processing unit (CPU) processor, a chip or any suitable computing or computational device, an operating system 3, a memory 4, executable code 5, a storage system 6, input devices 7 and output devices 8. Processor 2 (or one or more controllers or processors, possibly across multiple units or devices) may be configured to carry out methods described herein, and/or to execute or act as the various modules, units, etc. More than one computing device 1 may be included in, and one or more computing devices 1 may act as the components of, a system according to embodiments of the invention.

Operating system 3 may be or may include any code segment (e.g., one similar to executable code 5 described herein) designed and/or configured to perform tasks involving coordination, scheduling, arbitration, supervising, controlling or otherwise managing operation of Computing device 1, for example, scheduling execution of software programs or tasks or enabling software programs or other modules or units to communicate. Operating system 3 may be a commercial operating system.

Memory 4 may be or may include, for example, a Random Access Memory (RAM), a read only memory (ROM), a Dynamic RAM (DRAM), a Synchronous DRAM (SD-RAM), a double data rate (DDR) memory chip, a Flash memory, a volatile memory, a non-volatile memory, a cache memory, a buffer, a short term memory unit, a long term memory unit, or other suitable memory units or storage units. Memory 4 may be or may include a plurality of, possibly different memory units. Memory 4 may be a computer or processor non-transitory readable medium, or a computer non-transitory storage medium, e.g., a RAM. In one embodiment, a non-transitory storage medium such as memory 4, a hard disk drive, another storage device, etc. may store instructions or code which when executed by a processor may cause the processor to carry out methods as described herein.

Executable code 5 may be any executable code, e.g., an application, a program, a process, task or script. Executable code 5 may be executed by processor or controller 2 possibly under control of operating system 3. For example, executable code 5 may be an application that may perform screening tests for assessing a HS's behavior and/or development, perform or execute machine learning or neural network applications, etc. as further described herein. Although, for the sake of clarity, a single item of executable code 5 is shown in FIG. 1, a system according to some embodiments of the invention may include a plurality of executable code segments similar to executable code 5 that may be loaded into memory 4 and cause processor or controller 2 to carry out methods described herein.

Storage system 6 may be or may include, for example, a flash memory as known in the art, a memory that is internal to, or embedded in, a micro controller or chip as known in the art, a hard disk drive, a CD-Recordable (CD-R) drive, a Blu-ray disk (BD), a universal serial bus (USB) device or other suitable removable and/or fixed storage unit. Content may be stored in storage system 6 and may be loaded from storage system 6 into memory 4 where it may be processed by processor or controller 2. In some embodiments, some of the components shown in FIG. 1 may be omitted. For example, memory 4 may be a non-volatile memory having the storage capacity of storage system 6. Accordingly, although shown as a separate component, storage system 6 may be embedded or included in memory 4.

Input devices 7 may be or may include any suitable input devices, components or systems, e.g., a detachable keyboard or keypad, a mouse and the like. Output devices 8 may include one or more (possibly detachable) displays or monitors, speakers and/or any other suitable output devices. Any applicable input/output (I/O) devices may be connected to Computing device 1 as shown by blocks 7 and 8. For example, a wired or wireless network interface card (NIC), a universal serial bus (USB) device or external hard drive may be included in input devices 7 and/or output devices 8. It will be recognized that any suitable number of input devices 7 and output device 8 may be operatively connected to Computing device 1 as shown by blocks 7 and 8.

A system according to some embodiments of the invention may include components such as, but not limited to, a plurality of central processing units (CPU) or any other suitable multi-purpose or specific processors or controllers (e.g., processor or controllers similar element 2), a plurality of input units, a plurality of output units, a plurality of memory units, and a plurality of storage units.

According to some embodiments, a system for adaptively performing personalized or tailored screening tests for assessing a HS's behavior and/or development and detecting a condition of impeded behavior and/or development may, at a first stage, collect or gather data that may correspond to a behavioral and/or DC of a user. The data may be processed and classified, to determine a suspected condition, disease, syndrome, etc. related to a behavioral and/or developmental impediment. System 10 may subsequently select and present a test to the user. The test may be customized for the specific user and may be configured to provide information regarding the user's behavior and/or DC in view of the suspected impediment. At a later stage, the results of the test may be analyzed in conjunction with the gathered data, to determine whether the user indeed suffers from the suspected impediment and/or provide a recommendation for treatment of the determined impediment.

Figure 2:
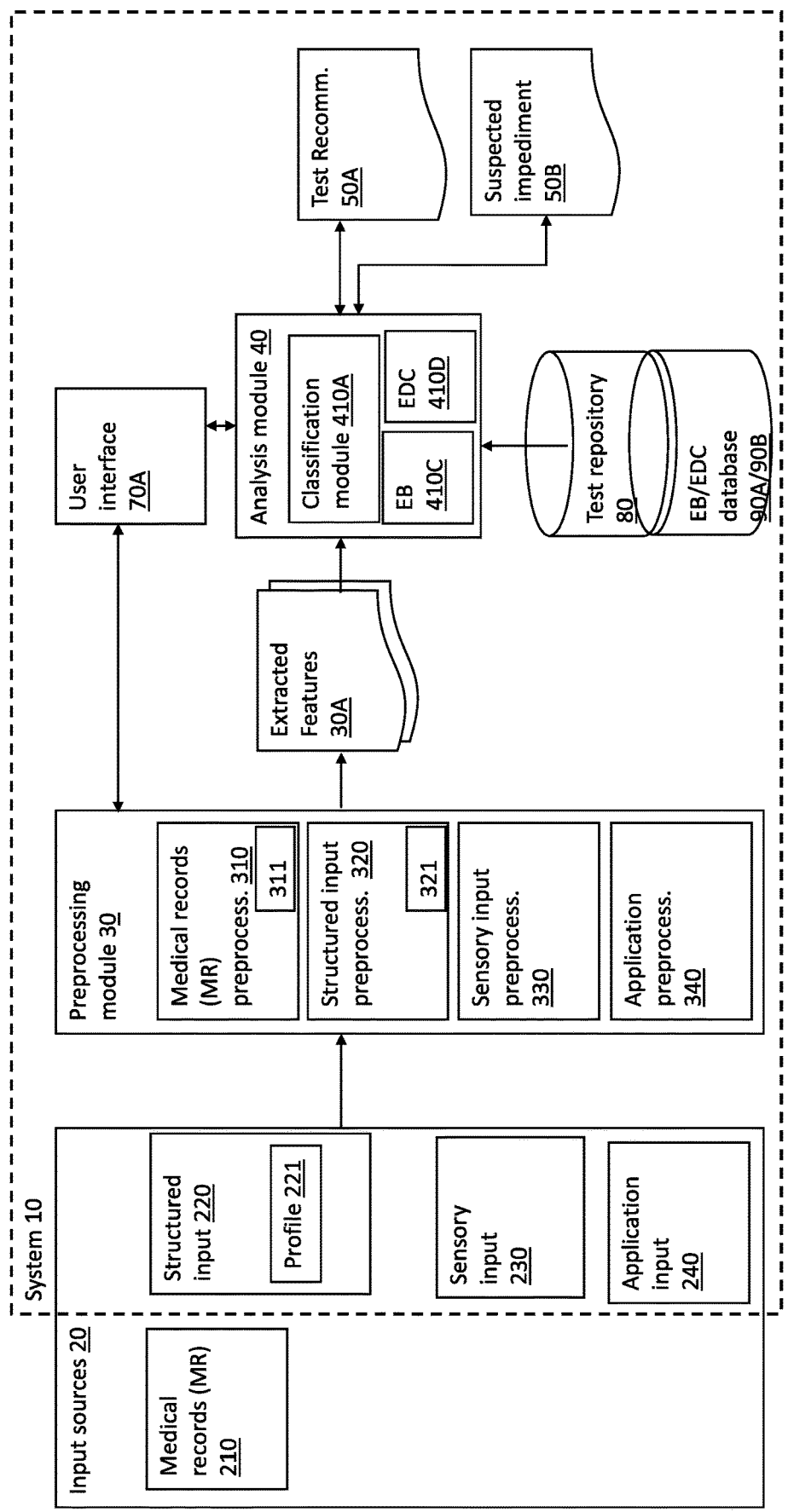
FIG. 2 is a block diagram, depicting a system for performing at least one of: assessing a human subject's behavior and/or development, adaptively performing personalized screening tests for diagnosing a developmental condition of the human subject and detecting a condition of impeded development, according to some embodiments.

Reference is now made to FIG. 2, which is a block diagram, depicting a system 10 for diagnosing a DC of the HS, according to some embodiments. System 10 may be or may include at least one computing device (e.g., element 1 of FIG. 1), including one or more processors, adapted to perform one or more embodiments of methods of the present invention.

System 10 may include one or more first computing devices (e.g., element 1 of FIG. 1), configured to obtain or collect one or more data elements, that may include information that may be indicative of at least one of: a HS's profile, a HS's behavior, the HS's DC and/or the HS's environment (e.g., temperature at the user's vicinity).

System 10 may further include one or more second, remotely located computing devices (e.g., remotely located cloud servers, such as a System as a Server (SaaS) server). The one or more second computing devices may be communicatively connected (e.g., via any type of computer network) to the one or more first computing device. The one or more second computing devices may be configured to analyze the data collected by the one or more first computing devices and produce at least one output. The output may, for example, include a recommended tailored or personalized test, a diagnosis, and a treatment recommendation.

As shown in FIG. 2, system 10 may receive and analyze a plurality of data elements pertaining to or indicative of a user's behavioral and/or DC from a plurality of input sources 20.

In some embodiments of the present invention, system 10 may receive data that may be or may include medical records (MR) 210 (e.g., from a medical database) of the HS. Such information may, for example, be stored on one or more computing systems (such as element 1 of FIG. 1) of a hospital, a clinic a healthcare center and the like.

MR data 210 may include, for example, previous data and/or analysis (e.g., made by a physician, a healthcare professional, and the like) of at least one of a physical, intellectual, social and/or mental condition of the HS and may be indicative of a DC of the HS. For example, MR data 210 may include one or more data elements pertaining to historic growth metrics (e.g., evolution of the HS's weight and/or height over time). In another example, MR data 210 may include one or more data elements pertaining to a medical history of diagnosed physical, cognitive and/or mental diseases that the subject may have been diagnosed with. In another example, MR data 210 may include one or more data elements pertaining to sleeping pattern (e.g., obtained from a sleep laboratory). In another example, MR data 210 may include one or more data elements pertaining to a medical imagery result (e.g., a magnetic resonance imaging (MRI) scan, a computed tomography (CT) scan, an X-ray image and the like) conducted on the human subject. In another example, MR data 210 may include one or more data elements pertaining to genetic and/or epigenetic information obtained from a sample (e.g., blood, saliva, etc.) belonging to the human subject.

As elaborated herein, system 10 may be or may include at least one computing device (e.g., element 1 of FIG. 1) that may include one or more input devices 7 and/or output devices 8, as elaborated in relation to FIG. 1. For example, system 10 may include a computing device (e.g., element 1 of FIG. 1) such as smart device (e.g., a smartphone), and the one or more input devices 7 and/or output devices 8 may include at least one user interface (UI) 70A, such as a touchscreen, adapted to present information to a user, and obtain information therefrom.

Additionally, or alternatively, system 10 may include or store one or more input sources 20. For example, system 10 may present to a HS (e.g., via UI 70A) one or more structured forms, adapted to obtain information pertaining to the HS's behavioral and/or DC. The HS (or a guardian thereof, such as their parents) may fill the one or more structured forms, to produce at least one structured input data element 220 (e.g., a structured text document) that may be indicative of their DC. System 10 may store the at least one structured input data element 220 (e.g., on a database, such as storage element 6 of FIG. 1) for further analysis.

Additionally, or alternatively, system 10 may include one or more sensors 230, including for example: wearable sensors, environment sensing devices, and the like. Data input sources 20 may include sensory input data that may originate from one or more sensors 230.

Sensor 230 may be adapted to sense or obtain at least one physical property data element that may be indicative of a behavior of the human subject.

For example, the at least one physical property data element may include data pertaining to the HS's behavior, cognitive condition, emotional, mental, physical condition and performance and/or reactions to presented conditions; data pertaining to a temporal physical condition of the HS (e.g., their temperature, skin pH, heart rate, etc.); and data pertaining to an environmental condition that may exist in the physical surroundings of the HS (e.g., room temperature, lighting, time of day, etc.).

Figure 3:
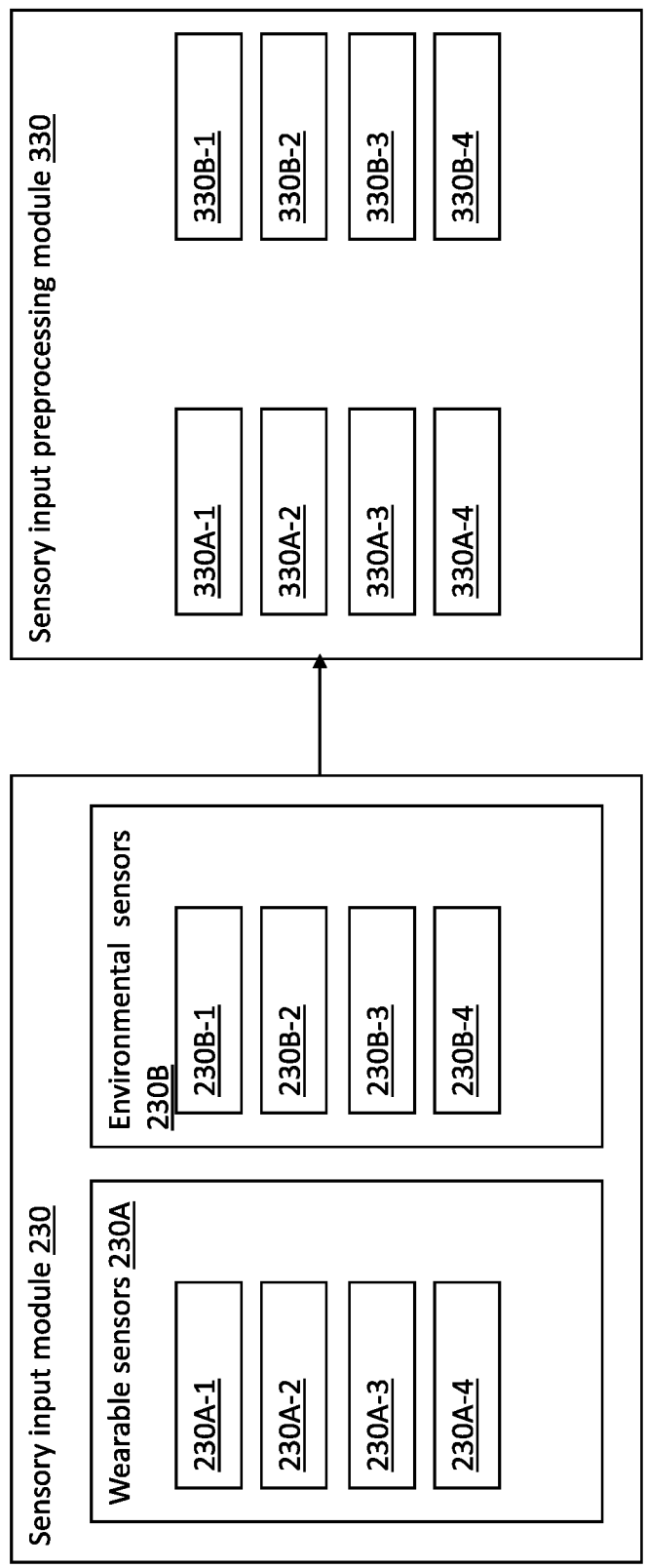
FIG. 3 is a block diagram, depicting a sensory input module and a respective sensory input preprocessing module that may be included in a system for diagnosing a developmental condition of the human subject, according to some embodiments.

The different types of sensors 230 and respective sensory input data elements are elaborated herein, in relation to FIG. 3.

Additionally, or alternatively, system 10 may be or may include one or more computing devices (e.g., element 1 of FIG. 1), such as a laptop computer, a smartphone, a tablet computer and the like. System 10 may include one or more sensors (e.g., input element 7 of FIG. 1) and may be configured to run or execute an application (e.g., element 5 of FIG. 1) by one or more processors (e.g., element 2 of FIG.

1). Application 5 may be adapted to obtain from the one or more sensors 7 at least one data element, such as a behavioral data element (e.g., application input 240) that may be indicative of a behavior and/or DC of the HS.

Application 5 may be of one or more types, selected from a list that may include one or more of: a non-spontaneous, interactive application (NIA); a spontaneous, non-interactive application (SNA); and a spontaneous, interactive application (SIA).

As implied by its name, an NIA application may be executed by system in a non-spontaneous manner (e.g., in response to a request, made by a user, to perform a test or an evaluation of a HS's behavioral and/or DC), and may be interactive in a sense that it may present information to a user (e.g., by a user interface (UI), prompt the user to interact with the presented information, and receive respective information therefrom.

For example, a HS may interact with an application 5 that may be executed or may be run on a computing device 1. Application 5 may be configured to collect data that may be indicative of the HS's behavioral and/or DC and/or data pertaining to a temporal condition of the HS. For example, the application may prompt a user to participate in a game of dexterity (e.g., a computer game), and may collect information regarding the user's performance in relation to typical performance expected and/or their condition in the game. The collected information may include, for example, data that may be indicative of the user's response time, their attentiveness, alertness, judgment and the like.

As implied by its name, an SNA application 5 may be executed by system in a manner that is non-interactive and spontaneous.

The SNA application 5 may be non-interactive in a sense that it may not require the user to interact or respond to data that may or may not be presented by the application. For example, computing device 1 may be a smart device, such as a smartphone, that may be used by the human subject, for example to view a video sequence (e.g., on a screen of the smartphone) or perform any other action associated with the smartphone, such as to conduct a phone conversation. SNA application 5 may use one or more resources of the computing device 1 (e.g., a camera, a microphone, an accelerometer, etc.) and/or sensors associated with or connected to computing device 1 (e.g., a skin pH sensor, a thermal sensor, a camera and/or any other sensor of a physiological property) to obtain one or more data elements pertaining to the human subject behavior (e.g., data pertaining to facial expressions, sounds, movement data, eye gaze and/or any physiological property), while the human subject is passively (e.g., non-interactively) observing the video.

The SNA application may be spontaneous in a sense that it may not require an explicit request to operate (e.g., to start collecting data at a specific point in time), may be executed in the background (e.g., in a manner that may not be detectable by the user and/or disruptive for their interaction with the computing device), and/or facilitate normal, uninterrupted operation of the computing device (e.g., by talking on the smartphone, reading and/or writing text messages thereon, browsing the internet, watching videos and the like).

As implied by its name, an SIA application 5 may be executed by system in a manner that is interactive and spontaneous. For example, an SIA application may allow normal interaction or operation of a computing device by a user (e.g., use their smartphone to conduct a phone call), and may prompt the user to interact or provide information regarding their operation of the computing device. For example, application 5 may detect a change in the volume of speech during a phone conversation and may prompt the user to provide information regarding their mental condition (e.g., anxious, happy etc.) following the call.

Application 5 may employ one or more resources and/or sensors of the computing device 1 to collect data corresponding to the user's operation or usage of the computing device. For example, computing device 1 may be a smartphone, and application 5 may employ resources of the smartphone, including for example one or more of the smartphone's camera, microphone, accelerometer and the like.

For example, application 5 may: record the user's voice when they are speaking on the smartphone; take a picture of the user (e.g., a 'selfie') during handling of a task (e.g., while the user is writing an email); monitor a gyroscope and/or an accelerometer that may be associated with or included in the computing device (e.g., the smartphone) to obtain data elements relating to the movement and/or position of the computing device during handling of a task (e.g., while the user is surfing the internet), and the like.

According to some embodiments, system 10 may include a preprocessing module 30, adapted to receive one or more data elements from one or more input sources 20. The one or more data elements may include, for example: data pertaining to medical records from MR 210; data pertaining to structured input 220 (e.g., one or more profile data elements pertaining to the HS); data pertaining to sensory input 230 (e.g., behavioral data elements that may include information indicative of a behavior of a HS from one or more sensors); and data pertaining to application input 240 (e.g., behavioral data elements that may include information indicative of a behavior of a HS from one or more computing devices such as a smartphone).

Preprocessing module 30 may extract one or more features 30A from the received data, pertaining to the specific characteristics of each data element. For example, data of sensory input 230 may include a reading from an accelerometer that may be worn by the HS. Preprocessing module 30 may extract at least one feature 30A of movement therefrom, including for example the repetitiveness of the HS's motion, the extent of their motion (e.g., how strong the movement is), the timing of their motion (e.g., in relation to a condition that may be presented by application 5 on their computing device), etc.

The one or more extracted features 30A may be analyzed by an analysis module 40, as elaborated herein, to determine a behavior and/or a DC of the HS and identify a suspected developmental impediment 50B that the HS may be suffering from. Analysis module 40 may subsequently recommend a treatment 50A against the identified developmental impediment, as elaborated herein.

In some embodiments, preprocessing module 30 may include an MR preprocessing module 310, configured to extract one or more features from MR 210 data.

MR preprocessing module 310 may be or may include a natural language processing (NLP) module 311, as known in the art. NLP module 311 may be configured to extract one or more features or data elements (e.g., words and/or phrases) that may be indicative of at least one of a historical physical, intellectual, cognitive, social and/or mental condition of the HS, including for example: previous physical, cognitive, intellectual, behavioral, emotional, social and/or mental tests, examinations and/or treatments that the HS may have undergone, a previous diagnosis that has been provided by a physician or a healthcare professional and the like.

In some embodiments, preprocessing module 30 may include a structured input preprocessing module 320, configured to extract one or more features 30A from structured input data 220. For example, structured input data 220 may be or may include a form that may have been filled by the HS and/or by another person on their behalf (e.g., by a parent or a guardian). The form may include for example, at least one data element pertaining to the HS's profile and/or at least one data element pertaining to a suspected behavior and/or a developmental impediment which may be the subject of inquiry by system 10. Structured input preprocessing module 320 may be configured to receive the form and extract the at least one feature 30A or data element therefrom.

The at least one profile parameter data element may be selected from a list that may include for example, a name, a gender, an age, a grade which the HS attends, data pertaining to a social condition (e.g., a school and/or another social environment which the HS attends, information pertaining to social relations, such as the quantity and quality of social ties and friends, an ethnic group to which the HS pertains, a financial status or condition of the HS and the like. The at least one data element pertaining to a suspected impediment may be for example a physical, cognitive, intellectual, behavioral or mental ailment or condition which the HS is known to or is suspected to be suffering from, including for example, autism, Asperger syndrome, Down syndrome, intellectual disability, dyslexia, Attention Deficit Hyperactivity Disorder (ADHD), brain injury, anxiety disorders and the like.

In some embodiments, structured input preprocessing module 320 may include an NLP module 321, as known in the art. NLP module 321 may be configured to extract one or more features or data elements (e.g., words and/or phrases) that may be pertain to the HS's profile and/or may be indicative of a suspected impediment.

In some embodiments, preprocessing module 30 may include a sensory input preprocessing module 330, configured to extract one or more features from sensory input data 230, as elaborated herein.

Reference is now made to FIG. 3, which is a block diagram, depicting a sensory input module 230, and a respective sensory input preprocessing module 330, which may be included in a system for diagnosing a DC of the HS, according to some embodiments.

As shown in FIG. 3, sensory input module 230 may include or may be connected or associated with one or more sensors (e.g., elements 230A-1 through 230A-4 and 230B-1 through 230B-4) that may each be configured to sense a physical property (e.g., a movement) of the HS and/or their surrounding environment (e.g., an ambient temperature) and produce at least one data element pertaining to the sensed physical property.

Sensory input preprocessing module 330 may include one or more sub modules, (e.g., elements 330A-1 through 330A-4 and 330B-1 through 330B-4) that may each be configured to preprocess a data element produced by a respective sensor, and extract therefrom at least one feature pertaining to the physical property of the HS (e.g., a frequency and/or extent of movement) and/or their surrounding environment (e.g., an extremity of an ambient temperature).

As shown in FIG. 3, sensory input module 230 may include one or more wearable sensors 230A (e.g., elements 230A-1 through 230A-4), that may be worn by the HS. The one or more wearable sensors may be configured or adapted to sense a physical property of the HS that may be selected from a list including one or more of: skin temperature, skin moisture, skin pH, skin conductivity, spectral distribution of skin color, pulse rate, blood pressure, movement, acceleration, firmness of touch and brain wave signals.

For example, a wearable sensor (e.g., element 230A-1) may be or may include a skin conductivity sensor, configured to measure the conductivity of a HS's skin surface, as known in the art. A respective sensory input preprocessing module (e.g., element 330A-1) may be configured to extract one or more features 30A from the skin conductivity data. For example, sub module 330A-1 may detect a condition of a skin conductivity outlier, e.g., when skin conductivity is well beyond the normal levels that may have been previously measured for the same HS, thus indicating that the HS may be perspiring.

In another example, a sensor which may be or may not be wearable (e.g., element 230A-2) may be or may include a thermometer, configured to measure the temperature of the skin of the HS. A respective sensory input preprocessing module (e.g., element 330A-2) may be configured to extract one or more features 30A from the thermometer, including for example the temporal temperature of the HS's skin and or an outlier of the HS temperature in relation to their normal temperature (e.g. detect a condition of a fever).

In another example, a sensor which may be or may not be wearable (e.g., element 230A-3) may be or may include a skin pH sensor, configured to measure the pH level of the HS's skin. A respective sensory input preprocessing module (e.g., element 330A-3) may be configured to extract one or more features 30A from the pH sensor, including for example the temporal pH of the HS's skin and or an outlier of the pH in relation to their normal pH (e.g. detect an abnormal pH condition).

In another example, a sensor which may be or may not be wearable (e.g., element 230A-4) may be or may include a moisture sensor, configured to measure the moisture or humidity of the skin of the HS. A respective sensory input preprocessing module (e.g., element 330A-4) may be configured to extract one or more features 30A from the moisture sensor, including for example an indication that the HS may be sweating excessively.

In another example, a sensor which may be or may not be wearable (e.g., element 230A-4) may be or may include a spectrometer, configured to measure the spectral distribution of the skin, or a portion thereof, of the HS. A respective sensory input preprocessing module (e.g., element 330A-4) may be configured to extract one or more features 30A from the spectrometer, including for example an estimated level of blood oxidation, as known in the art. (e.g., indicating HS oxygen levels related to metabolism).

In another example, a wearable sensor (e.g., element 230A-4) may be or may include a brain wave sensor, configured to measure brain signals (e.g., brain wave oscillations) of the HS. A respective sensory input preprocessing module (e.g., element 330A-4) may be configured to extract one or more features 30A from the brain wave sensor, including for example a condition of the HS's alertness, as known in the art.

In another example, a wearable sensor (e.g., element 230A-4) may be or may include a pulse meter, configured to measure the pulse rate of the HS. A respective sensory input preprocessing module (e.g., element 330A-4) may be configured to extract one or more features 30A from the pulse meter, including for example the temporal pulse rate and/or a pulse rate outlier (e.g., indicating that the HS may be in state of anxiety or excitation).

In another example, an wearable sensor (e.g., element 230A-4) may be or may include a blood pressure sensor, configured to measure the blood pressure of the HS. A respective sensory input preprocessing module (e.g., element 330A-4) may be configured to extract one or more features 30A from the blood pressure sensor, including for example the temporal blood pressure and/or a blood pressure outlier (e.g., indicating levels of stress experienced by the HS).

In another example, a sensor which may be or may not be wearable (e.g., element 230A-4) may be or may include a gyroscope and/or an accelerometer, configured to measure a movement and or an acceleration of the HS. A respective sensory input preprocessing module (e.g., element 330A-4) may be configured to extract one or more features 30A from the gyroscope and/or an accelerometer, including for example at least one movement parameter or feature 30A such as an smoothness of a movement, an extent of a movement, a pattern (e.g., a tremor) in a movement and the like.

In yet another example, a sensor, which may be or may not be wearable (e.g., element 230A-4) may be or may include a pressure sensor and may be configured to measure, for example a firmness and/or quality of a HS's grip and/or touch. A respective sensory input preprocessing module (e.g., element 330A-4) may be configured to extract one or more features 30A from the pressure sensor, including for example a firmness of a user's grip and quality of touch, a hand-eye connection, a level of motoric coordination, and the like.

In another example, a sensor which may be or may not be wearable (e.g., element 230A-4) may be or may include a camera (e.g., a camera of a smartphone), configured to capture an image and/or a video of the HS. A respective sensory input preprocessing module (e.g., element 330A-4) may include an image processing engine, configured to extract one or more features 30A from captured image, including for example at least one data element pertaining to a facial expression of a HS, a gaze of a HS, a movement of the HS, and the like. The term 'gaze' may refer herein, in the context of the one or more extracted features 30A, to any data element that may pertain to an HS's gaze or observation, including for example, a direction of observation, a duration of observation (e.g., in a given direction), a course of a point of focus, a pattern of eye movement, repetition of movement of a point of focus along one or more courses, and the like.

As shown in FIG. 3, sensory input module 230 may include one or more environment or ambience sensors 230B (e.g., elements 230B-1 through 230B-4), that may be configured to sense and/or monitor one or more physical property of the ambience in the vicinity of the HS. The one or more physical property may be selected from a list that may include one or more of: an ambient temperature, ambient moisture or humidity, an ambient lighting, etc.

For example, a first environment or ambience sensor (e.g., element 230B-1) may be or may include a lighting sensor, configured to measure the ambient light. A respective sensory input preprocessing module (e.g., element 330B-1) may be configured to extract one or more features 30A from the lighting data including for example the level of ambient light at the HS's vicinity.

In another example, a second environment or ambience sensor (e.g., element 230B-2) may be or may include a temperature sensor, configured to measure the ambient temperature. A respective sensory input preprocessing module (e.g., element 330B-2) may be configured to extract one or more features 30A from the temperature data including for example the temperature at the HS's vicinity.

In another example, a third environment or ambience sensor (e.g., element 230B-3) may be or may include a moisture or humidity sensor, configured to measure the ambient moisture or humidity. A respective sensory input preprocessing module (e.g., element 330B-2) may be configured to extract one or more features 30A from the humidity data including for example the humidity at the HS's vicinity.

In some embodiments, preprocessing module 30 may include an application input preprocessing module 340, configured to extract one or more features 30A from application input data 240, as elaborated herein.

Figure 4:
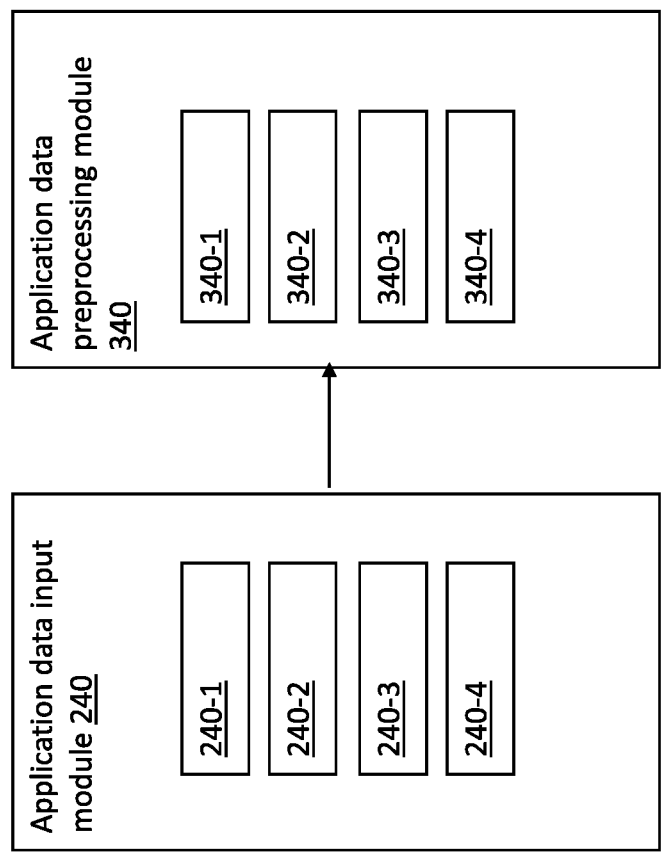
FIG. 4 is a block diagram, depicting an application input module and a respective application input preprocessing module, which may be included in a system for diagnosing a developmental condition of the human subject, according to some embodiments.

Reference is now made to FIG. 4, which is a block diagram, depicting an application input module 240 and a respective application input preprocessing module 340, which may be included in a system for diagnosing a DC of the HS, according to some embodiments.

As elaborated herein, system 10 may be or may include at least one computing device 1 (e.g., a smartphone, a tablet computer, a laptop and the like), configured to execute (e.g., by one or more processors, such as element 2 of FIG. 1) an application (e.g., element 5 of FIG. 1) Application 5 may be configured to obtain or produce from the one or more sensors (e.g., input elements 7 of FIG. 1) of the computing device at least one application input data element 240 (e.g., 240-1 through 240-4), that may be indicative of a behavior and/or DC of the HS.

Application data preprocessing module 340 may include one or more sub modules, (e.g., elements 340-1 through 340-4) that may be configured to preprocess a respective data element 240 produced by application 5 and may extract therefrom at least one feature pertaining to the physical aspect or property of the HS.

In some embodiments, application 5 may be an interactive application (e.g., a NIA-type application or an SIA-type application) and may be configured to record a voice of the HS during presentation of the application on a user interface (e.g., UI 70A) of a computing device 1 (e.g., a smartphone), for example, as part of a standard, screening test.

Alternatively, application 5 may be a non-interactive application and may be configured to record a voice of the HS during a normal operation of the computing device by the HS (e.g., during a phone call on the smartphone).

One or more application data preprocessing modules (e.g., 340-1) may be configured to analyze the recorded voice and obtain at least one acoustic/vocal parameter or feature 30A that may be indicative of a behavior and/or a DC. For example, module 340-1 may include a speech analysis engine, configured to detect one or more speech impairments or disorders as known in the art, such as an abnormal pattern or tone of speech that may be manifested, for example as a stutter or a lisp, a voice disorder that may include abnormal voice pitch and/or volume, an apraxia of speech, and the like. The one or more acoustic features 30A may be used by system 10 to diagnose a developmental condition (DC) or impediment of the HS, as elaborated herein.

According to some embodiments, at least one behavioral data element may be at least one picture of the HS or a portion thereof that may be indicative of the HS behavior. Application 5 may be configured to take the at least one picture of the HS during for example, presentation of the application on the UI or during a normal operation of the computing device by the HS.

For example, application 5 may be an interactive application (e.g., a NIA-type application or an SIA-type application) and may be configured to obtain or take a picture (e.g., a 'selfie') of the HS during presentation of the application on a user interface (e.g., UI 70A) of a computing device 1 (e.g., a smartphone). Alternatively, application 5 may be a non-interactive application and may be configured to take the picture during a normal operation of the computing device by the HS (e.g., while playing a game on smartphone).

One or more application data preprocessing modules (e.g., 340-2) may be configured to analyze the picture and obtain at least one visual or image related parameter or feature 30A that may be indicative of a behavior and/or DC of the HS. For example, module 340-2 may include a face-recognition engine, adapted to extract at least one of: a gaze of the HS to a specific point on the UI, a maintenance of eye-contact of the HS with a specific point on the UI (e.g., maintenance of eye-contact with a character, such as a human, a cartoon or an animal presented on the UI), a facial expression of the HS, and the like. The one or more visual features may be used by system 10 to diagnose a developmental condition (DC) or impediment of the HS, as elaborated herein.

According to some embodiments, at least one data element may be a movement of the HS, that may indicative of the HS behavior. Application 5 may be configured to monitor at least one movement of the human subject during, for example, presentation of the application on the UI (e.g., as part of performing a standard screening test), or during a normal operation of the computing device by the HS.

For example, application 5 may be an interactive application (e.g., a NIA-type application or an SIA-type application) and may be configured to monitor at least one movement of the HS by at least one sensor (e.g., an accelerometer, a camera, a gyroscope sensor, etc.) during presentation of the application on a user interface (e.g., UI 70A) of a computing device 1 (e.g., a smartphone). Alternatively, application 5 may be a non-interactive application and may be configured to monitor the movement during a normal operation of the computing device by the HS (e.g., while taking a picture on the smartphone camera).

One or more application data preprocessing module (e.g., 340-3) may be configured to analyze the monitored movement data and obtain at least one movement parameter that may be indicative of a behavior and/or DC. For example, module 340-3 may be adapted to identify or extract one or more movement parameters or features 30A including for example patterns and/or repetitiveness of movements (e.g., shaking, hand flapping, head banging and/or any stereotypic movement disorder, as known in the art), extent of movements, and the like. The one or more movement features 30A may be used by system 10 to diagnose a developmental condition (DC) or impediment of the HS, as elaborated herein.

Reference is now made back to FIG. 2. According to some embodiments of the present invention, system 10 may include an analysis module 40, configured to receive one or more data elements and/or features 30A from preprocessing module 30, corresponding to a respective one or more data elements originating from input sources 20. Analysis module 40 may be configured to analyze the plurality of data elements or features 30A to assess, evaluate or ascertain a suspected impediment of development of the HS.

According to some embodiments, analysis module 40, may be configured to receive one or more data elements or features 30A pertaining to a specific HS, from preprocessing module 30, including for example: MR records 210 data (e.g., medical records of the HS's developmental condition); structured input 220 data (e.g., one or more profile data elements or parameters, one or more data elements pertaining to social background); and sensory input 230 and/or application input 240 data (e.g., data indicative of a HS's behavior).

Analysis module 40 may analyze the one or more data elements or features 30A, such as features pertaining to the HS's behavior (e.g., repetitiveness of movement, high pitched or loud voice, quality of touch, eye contact etc.) and features pertaining to the HS's DC (e.g., from MR 210) in view of the one or more profile data elements (e.g., the HS's age and gender), to determine or obtain a diagnosis of a DC and/or a suspected impediment of development of the HS, as elaborated herein.

The following table, Table 2, includes an empiric example of a developmental impediment such as autism. The non-limiting example included in Table 2 may serve as a reference to show the symptoms pertaining to the specific developmental impediment (e.g., autism) and the respective plurality of behavioral features 30A that may be indicative of the HS's developmental impediment.

TABLE 2

| Symptom | Sensory input | Behavioral feature 30A |
|---|---|---|
| Lack of eye contact | Camera input: gaze estimation Depth mapping of pixels | Feature 30A may include a recording and analysis of the HS gaze, fixation and gaze pattern such as testing pupil direction, length and duration of focus including eye jitter and blinking identifying unusual or atypical response. |
| Lack of social communication | Camera input: Facial landmarks Depth mapping of pixels | Feature 30A may include an analysis of facial movements and/or gestures such as a smile, an indication of unusual or lack of movement, an indication of facial tics and distortions. Feature 30A may include facial expression processing and analysis to identify extreme or inappropriate behavior. |

TABLE 2-continued

| Symptom | Sensory input | Behavioral feature 30A |
| --- | --- | --- |
| Diameter of head (slight increase of head circumference) | Camera Facial landmarks | Feature 30A may include an analysis of measurement and/or distances of facial features such as the distance from the hairline to the chin, the width between eyebrows, the width between the eyes, etc., and an indication of one or more unusual measurement of facial features. |
| Lack of social communication and interactions, Atypical eye-hand contact and coordination | Touch 3d touch, force touch, pointer pressure | Feature 30A may include a recording and/or analysis of reaction or non-reaction to stimuli encouraging touch of screen a screen, such as location, diameter, proximity, lengths, strength and quality of touch on screen and/or device. This reaction may indicate lack of playfulness, likelihood to engage alone, etc. |
| Hypo/hyper sensitivity | Touch 3d touch, force touch, pointer pressure | Feature 30A may include a recording and/or analysis of the quality of touch such as pressure, accuracy, length, stability etc. Feature 30A may further include an indication of an identified unusual response. |
| Lack of social communication and interactions | ambience sensor | Feature 30A may include a recording and/or analysis of a computing device's screen and/or lighting sensitivity due to absence of reaction by a user and/or a lack of engagement by the user. |
| Lack of Speech Odd vocal - rhythm, pitch volume or tone of voice | Microphone Audio Input/output | Feature 30A may include a recording and/or analysis of acoustic signals, including a spectrum of frequencies, an identification of pre-verbal vocalizations, speech patterns, speech repetition, and unusual vocal responses or absence of response to a presented condition (e.g., on UI 70A of the user's computing device). |
| Unstable vestibular system Stereotype movements such as flapping, head banging, etc. unusual gait such as awkwardness, toe walking, etc. | gyroscope and accelerometer | Feature 30A may include a recording and/or analysis of stability, stereotype movements, tracks movements and an evaluation of gross and/or fine motor skills. |
| Metabolic Evaluation (e.g., diet sufficiency) | PPM spectrometer | Feature 30A may include a recording and/or analysis of $CO_2$ emission, indication of oxygen levels, and an indication of oxygen levels related to metabolism. |
| Anxiety and stress disorders | EEG PPG | Feature 30A may include a recording and/or analysis of heart rate, in relation to standard or spontaneous content presented on the HS computing device (e.g., smartphone). |
| Anxiety and stress disorders | Electro-dermal activity (EDA) | Feature 30A may include a recording and/or analysis of skin PH, temperature, moisture and/or conductivity in relation to standard or spontaneous content presented on the HS computing device (e.g., smartphone). |
| Anxiety and stress disorders incl. social anxiety, depression, ADHD, OCD, Mental disability Sleep disorders | Brain wave signals | Feature 30A may include an indication of neuro-physical health and/or stress levels in relation to standard or spontaneous content presented on the HS computing device (e.g., smartphone). |

TABLE 2-continued

| Symptom | Sensory input | Behavioral feature 30A |
|---|---|---|
| Anxiety and stress disorders | Blood pressure | Feature 30A may include a recording and/or analysis of blood pressure and/or stress levels in relation to standard or spontaneous content presented on the HS computing device (e.g., smartphone). |

According to some embodiments, analysis module 40 may include an expected behavior (EB) module 410C, configured to associate the HS to a group of HSs according to one or more profile parameters (e.g., age, gender, social background, etc.), and provide one or more indications of expected behavior in view of the HS's group association. EB module 410C may include or may be associated with an EB database 90A that may store one or more entries that associate between at least one group of HSs and one or more indications of expected, typical or normal behavior. The following table, Table 3, includes a plurality of simplified examples for association between a group characterized by having one or more specific profile parameter values (e.g., an age of a HS) and an expected behavior (EB).

TABLE 3

Expected behavior (EB) according to typical developmental milestones

| Age | Motor | Speech/Language | Social/Emotional |
|---|---|---|---|
| 0-2 months | Primitive reflex grasps | | Parent soothing |
| 3-4 months | Bats at object | Turns to voice<br>Cooing | Attachment child-parent |
| 5-6 months | Brings objects to midline<br>Rolls front-back - sometimes from curiosity, showing intention to reach something of interest | Squeals - shows engagement and happiness | Turn taking conversations<br>Exploring parents face |
| 6-8 months | Transfers hand to hand<br>Lack of transfer<br>Rolls both ways - to grab something wanted<br>Sits tripod - for play | Laughs out loud<br>Cries in special way- able to signal when hungry/tired (e.g., in contrast to absence of baby babble) | Distinguishes mother from others<br>Expresses emotions - happy, sad, angry<br>Social smile |
| 9-12 months | Pincer grasp (finger picks up cheerios, feeds itself cracker)<br>Pokes at objects<br>Gets from all 4s to sitting<br>Sits will hands free<br>Pulls to stand<br>Crawls | Specific mumbling - dada mama,<br>Responds to name - turn and looks (e.g., in contrast to not responding to their names by 12 months of age)<br>Gestures "bye bye"<br>Gestures game (e.g., peek a boo): shows engagement | Pushes things away that doesn't want<br>Reaches for familiar people |
| 12-14 months | Voluntary release<br>Throws objects - enhancing understanding of Cause and effect<br>Walks a few steps - wide based gait | Understands phrases like "no-no" or "all gone"<br>1 word with meaning (in addition to mama/dada) | Explores from secure base<br>Points at wanted items (e.g., in contrast to a condition in which the HS does not respond to name by 12 months of age, avoids eye-contact, and/or has flat or inappropriate facial expressions) |

TABLE 3-continued

Expected behavior (EB) according to typical developmental milestones

| Age | Motor | Speech/Language | Social/Emotional |
|---|---|---|---|
| 15-18 months | Walks well - demonstrating ability to reach where intends to go<br>Carries toys when walking | Points to show interest (e.g., in contrast to not pointing at objects and/or body parts by the age of 14 months | Shared attention<br>Points at interesting items to show parents<br>Shares toys with parents<br>Waves goodbye (e.g., in contrast to using few or no gestures, like not waving goodbye)<br>Plays social games, song games "patty cake", "peek a boo" |
| 19-24 months | Runs<br>Removes clothes<br>Tower of 4 blocks<br>Insists on doing things by self, such as feeding | Asks for food and drink using words or sounds | Increased independence<br>Parallel play (not trying to influence others)<br>Greets people with "hi"<br>Gives hugs and kisses |
| 2 years | Jumps on two feet<br>Up and down stairs<br>Opens door by turning knob | Speaks clearly and is understandable most of the time | Usually responds to corrections - stops<br>Shows sympathy to other children, tries to comfort them<br>Sometimes says "no"<br>Testing limits, tantrums, possessive (mine!) |
| 3 years | Climbing stairs alternating feet<br>Turns pages of books<br>Washes and dries hands | Asks why what where questions | Plays cooperatively with minimum conflict and supervision (e.g., in contrast to a condition in which the HS prefers to play alone, does not share interests with others, and/or only interacts to achieve a desired goal).<br>Plays games like hide and seek.<br>Roll play games.<br>Separates easily<br>Shares, shows empathy, plays cooperatively (e.g., in contrast to a condition in which the HS has difficulty in taking turns and sharing) |
| 4 years | Hops on one leg - at least three times<br>Goes downstairs alternating feet<br>Washes face without help | Answers questions such as "what do you do with your nose? Hands? Feet?<br>Tells a story | Protective towards younger children<br>"helps" with simple household tasks<br>Has preferred friend<br>Elaborate fantasy play |
| 5 years | Balance on one foot - at least 10 seconds<br>Skips<br>May ride a bike | Word play<br>Uses jokes or puns (e.g., in contrast to a condition in which the HS does not understand jokes, sarcasm, or teasing)<br>Phonemic awareness | Shows leadership among children.<br>Follows simple rules in board and card games.<br>Has a group of friends, follows group rules (e.g., in contrast to a condition in which the HS does not understand personal space boundaries, avoids or resists physical contact, is not comforted by others during distress And/or has trouble understanding other people's feelings or talking about their own feelings) |

Preprocessing module 30 may extract at least one behavioral feature 30A from a behavioral data element (e.g., originating from sensory input 230 and/or application input 240, as elaborated herein). Analysis module 40, may analyze at least one extracted behavioral feature 30A in view of at least one indication of a respective expected behavior (e.g., as elaborated in Table 2) as elaborated herein to ascertain whether the extracted feature 30A may indicate a normal or typical DC of the HS, or rather indicate a suspected developmental impediment.

For example, assume that:
(a) an indication of expected behavior for a HS of a specific profile (e.g., an age group) in reaction to a specific condition or stimulus (e.g., a presented video) may be or may include that the HS is expected to maintain eye-contact for a first, minimal period of time with an element (e.g., an image of a speaker) that may be included in the presented video; and
(b) a feature 30A of preprocessing module 30 may be or may include an indication that the maximal amount of time which the HS maintains eye contact with the speaker is a second period of time, shorter than the first period.

Analysis module 40 may analyze the difference between the expected behavior (e.g., minimal duration of eye contact) and the extracted respective feature (e.g., the actual duration of eye contact) to ascertain whether this discrepancy may indicate a developmental impediment, such as autism.

In another example, an indication of expected behavior for a HS of a specific profile (e.g., an age group) in reaction to a specific condition (e.g., a presented video or image of a character, such as a cute puppy) may be or may include that the HS is expected to gaze at a specific point in the image or video (e.g., the puppy's eyes). A feature 30A of preprocessing module 30 may be or may include an indication that the HS is gazing at a different point (e.g., focusing on eyebrows instead of eyes) or lack gaze altogether (e.g., express no relation or reaction to the cute puppy on screen).

In another example, an indication of an expected behavior for a HS of a specific profile (e.g., an age group) in reaction to a specific condition (e.g., the puppy image) may be or may include that the HS is expected to express a reaction to the presented condition, such as produce a facial expression (e.g., express a smile). A feature 30A of preprocessing module 30 may be or may include an indication that the HS's facial expression may be static, or indifferent to the presented condition.

According to some embodiments, analysis module 40 may include an expected developmental condition (EDC) module 410D, configured to associate the HS to a group of HSs according to one or more profile parameters (e.g., age, gender, social background), and provide one or more indications of an EDC in view of the HS's group association. EDC module 410D may include or may be associated with an EDC database 90B that may store one or more entries that associate between at least one group of HSs and one or more indications of an expected, typical or normal developmental condition.

The following table, Table 4, includes simplified examples for association between a group of HSs that may be characterized by having one or more specific profile parameter values (e.g., a group age of the HS) and an EDC.

TABLE 4

| | | Motor | Speech/ Language | Cognitive | Social/ Emotional |
|---|---|---|---|---|---|
| | | | Expected development according to typical developmental milestones | | |
| 0-2 months | | Primitive reflex grasps (e.g., in contrast to a condition in which the HS has problems with feeding or swallowing) | Primitive reflex suck Alerts to sound Startles to loud sounds | Visual Focal length 10' Prefers contrasts, face, high pitched voice | Parent soothing |
| 3-4 months | | Head steady when held Hands open half the time Palmer grasp reflex Bats at object | | Prefers usual caregiver | Attachment child-parent |
| 5-6 months | | Brings objects to midline Sits with support Rolls front-back | | Anticipates routines Purposeful sensory exploration of objects (eyes hands mouth) | Turn taking conversations Exploring parent's face |
| 6-8 months | | Lifts head when lying on stomach Racking grasp Transfers from hand to hand | | Stranger anxiety Looks for dropped or partially hidden object | Distinguishes mother from others Expresses emotions - happy, sad, |

TABLE 4-continued

Expected development according to typical developmental milestones

|  | Motor | Speech/Language | Cognitive | Social/Emotional |
|---|---|---|---|---|
|  | Rolls both ways (e.g., in contrast to a condition in which the HS does not roll from front to back) Sits tripod |  |  | angry Social smile |
| 9-12 months | Pincer grasp (finger picks up cheerios) Pokes at objects Gets from all 4s to sitting position. Sits hands free (e.g., in contrast to a condition in which the HS does not sit independently) Pulls to stand Crawls |  | Uncovers toy "peek-a-boo" | Pushes things away that doesn't want Reaches for familiar people |
| 12-14 months | Voluntary release Throws objects Walks a few steps - wide based gait Uses spoon, drinks from cup Walks around crib or furniture while holding on Crawls on hands and knees (e.g., in contrast to a condition in which the HS uses one hand exclusively, flaps hands, rocks body, spins in circles, etc.) |  | Cause an effect Trial and error Imitates gestures and sounds Uses objects functionally (roll toy car) | Explores from secure base Points at wanted items |
| 15-18 months | Walks well Not walking by 18 months Carries toys while walking Fisted pencil grasp | Demonstrates normal linguistic development (e.g., in contrast to a condition in which the HS demonstrates inferior language development, such as using only 5 words or less, presents delayed speech and language skills, does not utter single words by the age of 15 months, expresses disordered speech, expresses idiosyncratic speech, repeats words or phrases over and over (echolalia), reverses pronouns (e.g., | Looks for moved or hidden objects Experiments with toys to make them work | Shared attention Does not point or respond to pointing Points at interesting items to show parents Shares toys with parents Waves goodbye Plays social games, song games "patty cake", "peek a boo" (e.g., in contrast to a condition in which the HS avoids eye contact, prefers to remain alone, does not participate in roll playing or "pretend" games, etc.) |

TABLE 4-continued

Expected development according to typical developmental milestones

| | Motor | Speech/Language | Cognitive | Social/Emotional |
|---|---|---|---|---|
| | | says "you" instead of "I"), talks in a flat, robot-like, or sing-song voice, etc.) | | |
| 19-24 months | Runs well Kicks a ball forward Stands without support | Names a few familiar objects in books | Imitates house work Symbolic play (give teddy a drink) | Increased independence Parallel play (not trying to influence others) Greets people with "hi" Gives hugs and kisses (e.g., in contrast to a condition in which the HS presents abnormal attachment patterns, such as excessive or indiscriminate 'clinging') |
| 2 years | Jumps on two feet Up and down stairs | Has a vocabulary of at least 20 words. Talks in sentences at least four words long Uses I/me/you Uses plurals | New problem solving strategies (e.g., in contrast to a condition in which the HS expresses obsessive interests) | Usually responds to corrections - stops Shows sympathy to other children Testing limits, tantrums, possessive (mine!) |
| 3 years | Climbing stairs alternating feet Undresses Toilet trained Draws circles | 3 step command - follows a series of three instructions in order. (e.g., in contrast to a condition in which the HS gives unrelated answers to questions) | Simple time concepts Identifies shapes Compares two items (e.g. bigger) Counts to 3 | Plays cooperatively (e.g., in contrast to a condition in which the HS is easily upset by minor changes). Roll play. Shows empathy. Plays cooperatively |
| 4 years | Hops on one leg Down stairs alternating feet Draws X, diagonals Cuts shape with scissors Buttons | Talks in long complex sentences, more than 10 words. Past tense Tells a story | Opposites Identifies 4 colors Counts to 4 | Protective towards younger children "helps" with simple household tasks Has preferred friend Elaborate fantasy play |
| 5 years | Balance on one foot 10 seconds Skips May ride a bike Draw person - 10 body parts Copies name Independent hygienic activities (e.g., in contrast to a condition in which the HS manifests | 5000 words Counts ten objects Reads and prints a few letters and numbers | Recites ABC's Recognizes some letters Pre literacy and numeracy skills Counts to 10 accurately | Follows simple rules in board and card games Has friends (e.g., in contrast to a condition in which the HS has no friends, Plays stereotypically or immaturely, has trouble understanding other people's |

TABLE 4-continued

Expected development according to typical developmental milestones

| Motor | Speech/Language | Cognitive | Social/Emotional |
|---|---|---|---|
| delayed self-care, or unable to copy their own name) | | | feelings or talking about their own feelings) |

Preprocessing module 30 may extract at least one feature 30A pertaining to a DC that may originate for example, from an MR data element 210 and/or a structured input 220 data element, as elaborated herein. Analysis module 40 may analyze at least one feature in view of at least one indication of a respective expected DC as elaborated in Table 4, to ascertain whether the extracted feature 30A may indicate a normal or typical DC of the HS, or rather indicate a suspected developmental impediment.

For example, assume that:
(a) an indication of an EDC may be or may include a definition that a developmental condition of the HS (e.g., of 6 months of age) is expected to be able to perform specific actions, such as babble, smile and/or roll from their back side to his front side; and
(b) a feature 30A of preprocessing module 30 may be or may include an indication from a structured input 220 data element (e.g., a free-text report that may have been filed by the HS's parents) that may indicate that the HS does not perform such actions (e.g., babble sounds, smile or roll).

Analysis module 40, may analyze the difference between the expected DC and the extracted respective feature to ascertain whether this discrepancy may indicate a developmental impediment.

Additional examples to developmental conditions that may indicate a developmental impediment may include, for example: having unusual reactions to the way things sound, smell, taste, look, or feel; having unusual interests and behaviors, such as repetitively lining up toys or other objects; playing with toys the same way every time (e.g., concentrating on specific parts of objects such as wheels of a toy car); being excessively organized; being obsessively interested in specific elements or subjects; having to follow specific routines or thriving on routine; being hyperactive; being impulsive; having a short attention span; showing aggression; causing self-injury; having temper tantrums; having unusual eating and sleeping habits; having unusual mood or emotional reactions; lacking fear or experiencing abnormal levels of fear; having unusual sleeping habits; and having abnormal moods and/or emotional reactions (e.g., laughing or crying at unusual times or showing no emotional response at times such reactions may be expected).

According to some embodiments, analysis module 40 may analyze one or more behavioral and/or developmental data element and/or features by way of classification: analysis module 40 may include a classification module 410A, configured to receive as input at least one of: one or more behavioral data elements and/or features 30A; one or more indications of expected behavior (e.g., from EB module 410C); one or more developmental data elements and/or features 30A; one or more indications of expected DC (e.g., from EDC module 410D); and one or more profile data elements.

Classification module 410A may be configured to classify the HS according to the received data elements (e.g., one or more data elements or features 30A pertaining to behavior and/or DC) to one or more groups or classes of DCs. For example, one or more groups or classes of DCs may pertain to a typical or normal DC (e.g., in view of specific one or more profile parameters), and one or more groups or classes may pertain to one or more developmental impediments (e.g., Asperger syndrome, autism, Down syndrome, intellectual disability etc.).

Classification module 410A may classify the HS to one of the classes or groups (e.g., a class of a specific impediment such as autism, Asperger syndrome, Down syndrome, intellectual disability, dyslexia, attention deficit hyperactivity disorder (ADHD), brain injury, anxiety disorders, mental disability and the like), according to the one or more data elements and/or features 30A, and produce an indication of the respective suspected impediment 50B (e.g., the suspected Asperger syndrome).

According to some embodiments, classification module 410A may be or may include any type of a machine-learning (ML) based classification model as known in the art (e.g. a trained neural network), that may be adapted to classify DCs of HSs according to specific classes or groups, where each group is associated with one or more developmental impediment, including for example (e.g., autism, Asperger syndrome, Down syndrome, intellectual disability etc.)

In some embodiments, classification module 410A may be trained on a labeled training set of HSs to classify or categorize DCs of HSs according to classes of suspected developmental impediments, in a supervised training stage. The training stage may include a supervised learning process, as known in the art. For example, classification module 410A may be trained by a human expert, who may diagnose HSs as having one or more specific developmental impediments and label the HSs according to their diagnosis.

Classification model 410A may thus be trained to receive data elements or features 30A pertaining to behavioral and/or DCs of additional HSs from beyond the training set, and classify the additional HSs as members of one or more groups of DCs that may be associated with one or more respective developmental impediments.

According to some embodiments, subsequent to association or classification of a HS to one or more groups or classes of DCs by classification module 410A, analysis module 40 may present to the HS a personalized, recommended test 50A on a user interface (UI) of a computing device. Test 50A may be personally adapted to determine or diagnose a DC and/or a developmental impediment of the HS in view of the suspected impediment.

In embodiments where system 10 is not implemented on the same computing device as the computing device of the HS, analysis module 40 may communicate the recommended test 50A to the HSs computing device (e.g., smartphone) through any appropriate computer communication as known in the art.

The HS may be prompted to perform test 50A on the UI of their computing device, and test 50A may be selected or adapted according to the suspected impediment, so as to fine-tune the diagnosis of the suspected developmental impediment as elaborated herein.

As elaborated herein, embodiments of the invention may perform a screening test for diagnosing a DC of a human subject by using a processor of a smart device, such as a smartphone.

For example, a user may utilize the smartphone in a spontaneous, manner, such as performing a voice call, observing a video, viewing an image and/or listening to an audio sequence. An SNA application 5 may be adapted to obtain one or more behavioral data elements (e.g., one or more extracted behavioral features 30A elements of FIG. 2), comprising information that may be indicative of a behavior of a human subject, during the spontaneous, utilization of a smartphone, as elaborated herein (e.g., in relation to FIG. 2).

The term "spontaneous" may refer in this context, to any action that may be associated with a normal operation of the smartphone, such as performing a voice call, playing a game, looking at pictures, browsing the internet and/or viewing a video sequence. This is in contrast to a non-spontaneous operation of the smartphone, which may include any action or operation that may preconfigured to obtain the information indicative of the behavior of the human subject (e.g., a game or a video which may be adapted to invoke an emotional and/or physical sensation on the human subject).

Embodiments of the invention may subsequently analyze (e.g., by analysis module 40' of FIG. 2 and/or FIG. 5) the one or more behavioral data elements 30A to obtain a suspected impediment (e.g., element 50B of FIG. 2) of development of the human subject. Additionally, embodiments of the invention may present to the human subject, on a user interface, a personalized test (e.g., element 50A of FIG. 2), adapted to diagnose the developmental condition of the human subject, or obtain a diagnosis (e.g., element 60A of FIG. 5) in view of the suspected impediment 50A.

As elaborated herein, each group or class of DCs may be associated with one or more developmental impediment, and with one or more recommended test 50A corresponding to the suspected behavioral and/or developmental impediment. Following categorization of a HS's behavior and/or DC to a class of DCs, analysis module 40 may present the recommended test 50A to the HS on a user interface such as element 70A, according to the suspected impediment. For example, analysis module 40 may present on UI 70A a recommended test 50A that may be specifically adapted to determine a DC of the HS in view of the suspected impediment. In other words, recommended test 50A may be adapted to ascertain, in a high level of probability whether the HS is suffering from the suspected behavioral and/or developmental impediment.

For example, analysis module 40 may analyze the plurality of data elements of input sources 20 and/or features 30A of preprocessing module 30 (e.g., by classification module 410, as explained herein) and may determine that a HS may be suffering from a suspected developmental impediment 50B such as autism. Analysis module 40 may subsequently present (e.g., on UI 70A) a recommended test 50A test that may be adapted to identify or ascertain a condition of autism at the HS in a high reliability, and/or identify a sub-class of the developmental impediment (e.g., a sub-class of autism) which the HS may be suffering from.

According to some embodiments, system 10 may include or store a test repository 80 that may include one or more test templates. The one or more test templates may be adapted or designed by one or more expert diagnosticians, for diagnosing specific behavioral and/or developmental impediments.

Analysis module 40 may select one or more test templates that may correspond with a specific suspected developmental impediment. For example, in a case where the suspected developmental impediment may be autism, the selected test template may include a presentation of a video sequence, and the test template may be adapted to determine an HS's relation and/or interaction to the video, such as reacting by a facial expression (e.g., smiling), maintaining eye-contact with a character presented in the video, choosing to repeatedly play the video time and time again and the like.

In another example, in a case where the suspected developmental impediment may be dyslexia or dysgraphia, the selected test template may include a presentation of text (e.g., in audible and/or written form) and may be adapted to prompt the HS to read (e.g., out loud), choose and/or write (e.g., by an electronic pen) text so as to evaluate the HS's capabilities.

Analysis module 40 may adapt the selected test template according to the acquired data, such as the one or more data elements or features 30A (e.g., behavioral features) as explained herein and/or the one or more data elements pertaining to the HS's profile (e.g., age group, geographic location, etc.), to produce a test that may be tailored or personalized to the specific HS.

Pertaining to the example where the suspected developmental impediment may be dyslexia or dysgraphia, the test may be adapted to be in the spoken language of the HS's geographic location, and may be personalized or tailored to fit the HS's age group (e.g., correspond with the expected vocabulary of the HS's age).

Pertaining to the example where the suspected developmental impediment may be autism, the presented video may be adapted to include a video that may correspond with an expected interest of the HS's profile (e.g., a familiar cartoon, a familiar pet, a speaking doll for a year-old young child, an action-figure for a five year old child, and the like).

According to some embodiments, recommended test 50A may be interactively and adaptively tailored or personalized during the test process itself. For example, analysis module 40 may select a first recommended test for the HS as explained herein. Application 5 may present test 50A (e.g., on UI 70) for the HS to perform. The outcome of the performed test (e.g., an indication pertaining to the user's behavior in view of the presented test) may be introduced as additional input to analysis module 40 (e.g., to classification module 410A). Analysis module 40 may subsequently, interactively select or produce another recommended test 50A (e.g., to fine-tune a determination of suspected impediment 50B).

Recommended test 50A may be, for example, presented to the HS in one or more formats that may be suitable for diagnosing the suspected impediment, as known in the art. The format of recommended test 50A may be selected, for example, from a list that may include one or more of: a textual form that the HS may be prompted to fill; an interactive questionnaire, in which the HS may be prompted to respond to specific questions and/or conditions which may be presented to them; a game (e.g., a computer game) in which the HS may be required to partake; an image or a video which the HS may be expected to relate to and/or interact with in a specific way; an external device (e.g. a robot, VR, AR), and the like.

System 10 may obtain one or more profile data elements, including personal information regarding the HS (e.g., their name, age, gender, school grade, etc.) from one or more structured input 220. Analysis module 40 may adapt the presented test 50A, and personalize it according to the obtained one or more profile data elements. Adaptation of the test according to the one or more profile data elements may include for example: selecting test 50A (e.g., from a repository of tests 80) according to the subject's age, gender, etc.; using the subject's name in the test; adapting parameters of test 50A (e.g., the duration of the test, presented items in the test, etc.); adapting parameters of the EB expected from the HS (e.g., duration of eye contact, quality of touch, heartrate etc.) following presentation of test 50A; adapting parameters of the expected developmental condition (EDC), and the like.

For example, a test may include presentation of a video sequence to an HS on a UI of a hand-held computing device (e.g., a smartphone). The test may be adapted or selected to invoke a specific reaction or behavior (e.g., produce a smile, utter a word, moving the handheld device according to instructions etc.) from the HS. The test may be adapted according to the HS profile (e.g., the HS's age group) to examine whether the HS's behavior (e.g., smiling, babbling, movement or lack thereof) complies with one or more specific developmental conditions, corresponding with the HS's profile (e.g., as elaborated herein in relation to tables 3 and 4).

In another example, preprocessing module 30 may extract at least one feature 30A containing information corresponding to a temporal, environmental condition (e.g., temperature, lighting, time of day, etc.) at the HS's vicinity or environment from one or more sensory input 230. Analysis module 40 may adapt the presented test according to the obtained environmental data. For example, under the assumption that a HS's attentiveness may be influenced by their level of alertness or tiredness, analysis module 40 may adapt parameters of the EB (e.g., duration of eye contact) following presentation of test 50A according to the time of day (e.g., allow higher tolerance to shorted duration of eye contact when the test is conducted under poor lighting conditions or late in the evening).

In another example, preprocessing module 30 may extract at least one feature 30A containing information corresponding to a physical condition of the HS from one or more sensory input 230. Analysis module 40 may adapt the presented test according to the obtained data. For example, under the assumption that a HS's attentiveness may be influenced by their physical condition (e.g., a condition of excitation, manifested by a high level of heart rate), preprocessing module 30 may adapt the parameters of the EB (e.g., duration of eye contact) following presentation of test 50A according to the feature 30A of physical condition (e.g., allow higher tolerance to shorted duration of eye contact or shortened attention expansion when the HS is experiencing a high level of heart rate).

In another example, preprocessing module 30 (e.g., NLP module 311) may extract at least one feature 30A (e.g., a word or a phrase) containing information corresponding to a MR data element 210 of the HS (e.g., a historical record of a measured parameter of attentiveness, during a previous test performed by a physician). Subsequently, analysis module 40 may select a specific test 50A to ascertain whether the previous findings (e.g., short duration of eye contact) of the MR data element 210 are still viable, or whether a change has occurred in the HS's behavior.

In another example, preprocessing module 30 may extract at least one feature 30A pertaining to data that may correspond to a structured input of the HS. For example, NLP module 321 may extract at least one word or phrase pertaining to a DC of the HS (e.g., a report of the parents concerning lack of social connections of the HS). Subsequently, analysis module 40 may select a specific test 50A to ascertain whether the HS's behavior is one that corresponds with an empathic or expected social behavior.

Figure 5:
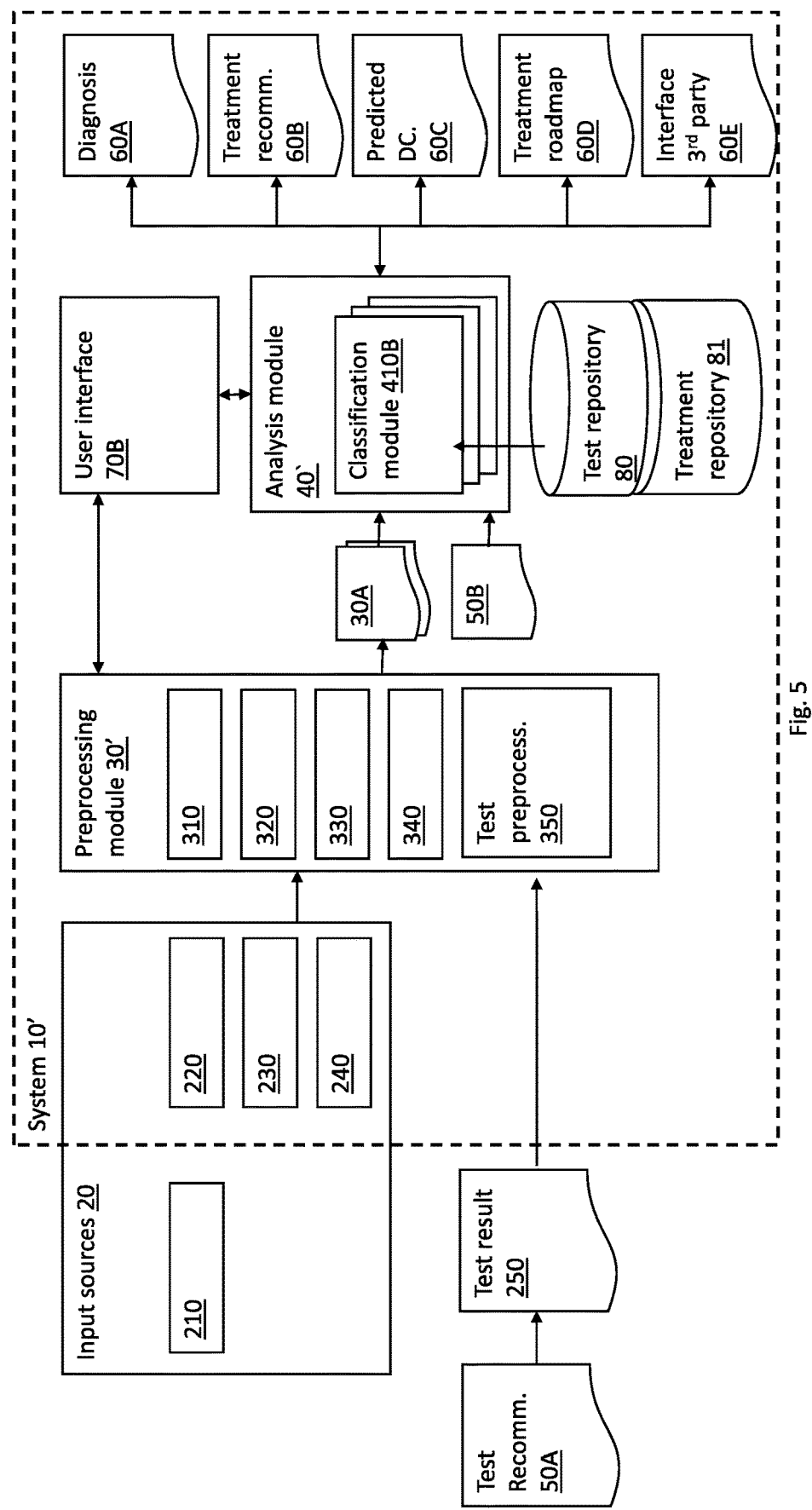
FIG. 5 is a block diagram, depicting a system for performing at least one of: assessing a human subject's behavior and/or development, adaptively performing personalized screening tests for diagnosing a developmental condition of the human subject and detecting a condition of impeded development, according to some embodiments.

Reference is now made to FIG. 5, which is a block diagram, depicting a system 10' for diagnosing a DC of the HS, according to some embodiments. As shown in FIG. 5, system 10' may include components that may be equivalent to components of system 10, as presented in FIG. 2, and will not be discussed here for the purpose of brevity. According to some embodiments, system 10' may be implemented on the same computing device (e.g., element 1 of FIG. 1) as that of system 10. Alternatively, system 10' may be communicatively connected (e.g., through the internet) with system 10, and may receive therefrom at least one input data element (e.g., elements 210, 220, 230, 240 and/or 250) and analyze the at least one input data element to ascertain whether the HS's behavior and/or DC indeed indicates that they may be suffering from the suspected developmental impediment (e.g., autism).

System 10' may be configured to receive as input at least one result (e.g., element 250) of personalized, recommended test 50A, and analyze result 250 (e.g., in view of the accumulated data as elaborated herein in relation to FIG. 3) to determine whether the HS indeed suffers, in high probability, from the suspected behavioral and/or developmental impediment.

System 10' may subsequently produce at least one output 60, including for example: a diagnosis 60A of the case; a recommended treatment 60B (e.g., a referral to medical care); a predicted developmental condition 60C; a report or roadmap of treatment 60D; and an interface for external, third-party administrative systems 60E, as elaborated herein.

As elaborated herein, system 10 may be configured to present to the HS a personalized test 50A on a computing device for example by an application on the UI of a user's smartphone. Following performance of personalized test 50A by the HS (e.g., on UI 70), system 10' may receive from the computing device one or more test input data elements 250 (e.g., behavioral data elements) that may include information that may be indicative of a behavior of the HS during the performance of personalized test 50A.

System 10' may include one or more test preprocessing modules 350 configured to extract one or more features 30A from the received test outcome 250. The one or more extracted features 30A may include, for example behavioral data elements that may have been measured by application 5 during performance of personalized test 50A, including for example: duration of eye-contact, focus of eye gaze, quality of touch, heart-rate, amount of movement of the HS's computing device, etc.

System 10' may include one or more analysis modules 40' that may be unique or dedicated for diagnosing a developmental condition of the HS in view of the suspected developmental impediment.

Analysis module 40' may be or may include one or more classification modules 410B. According to some embodiments, the one or more classification module 410B may be different from classification module 410A in a sense that whereas classification module 410A may screen a population of HSs, produce an initial diagnosis of suspected developmental impediment to one or more HS, and prompt the HS to perform a personalized test 50A, classification module 410B may be adapted to perform at least one of: reevaluate the initial diagnosis of classification module 410A in view of the outcome 250 of test 50A; fine-tune the classification of the HS to sub classifications within diagnosis of suspected developmental impediment; and present to the HS, for example, a customized, personalized method of treatment.

The one or more classification modules 410B may receive as input at least one data element, including for example: a first data element or feature 30A extracted from preprocessed data elements 310, 320, 330, and/or 340; a second data element or feature 30A extracted from preprocessed test data input 350 (e.g., pertaining to the result 250 of personalized test 50A); a third data element of feature 30A pertaining to a profile data element (e.g., the HS's age); and an indication of the suspected impediment 50B.

The one or more classification modules 410B may decide or predict the probability in which the HS suffers from the suspected impediment based on the at least one received data element, as elaborated herein. Analysis module 40' may subsequently produce a diagnosis of the DC of the HS and decide whether the HS indeed suffers from the suspected impediment. In some embodiments, the diagnosis of DC may include for example: the suspected impediment; a classification of the HS according to their DC, in view of the suspected impediment; a probability or a level of diagnosis certainty; and indication of one or more feature or data elements that may correspond to the suspected developmental impediment, as elaborated herein.

In some embodiments, at least one classification module 410B may be or may include a rule-based classifier (e.g. a trained neural network), configured to predict a probability in which a user may be suffering from the suspected behavioral and/or developmental impediment based on one or more of the preprocessed test results 350 and or preprocessed data elements 310, 320, 330, and 340.

For example, preprocessed test results 350 may include one or more features 30A pertaining to parameter values that may have been measured during the HS's performance of personalized test 50A, and may correspond to a behavior of the HS (e.g., duration of eye-contact, heart-rate, amount of movement of the HS's computing device, etc.). Analysis module 40' may identify at least one behavioral outlier, indicating a discrepancy between the one or more features 30A (e.g., short duration of eye-contact) and at least one respective EB (e.g., an expected range of duration of eye-contact). Rule-based classifier 410B may apply a weight to each measured feature 30A according to the identified discrepancy, and accumulate the weights to produce an overall score. Rule-based classifier 410B may determine whether the HS suffers from the suspected impediment according to the score. For example, if the overall score surpasses a first predefined threshold, then rule-based classifier 410B may determine that the HS suffers from the suspected impediment in a first probability and if the overall score surpasses a second, higher predefined threshold, then rule-based classifier 410B may determine that the HS suffers from the suspected impediment in a second, higher probability.

In another example, preprocessed test results 350 may include one or more features 30A pertaining to sensory input 230 that may have been measured during the HS's performance of personalized test 50A, and may correspond to an environmental data element (e.g., the time of day, the ambient lighting). Under the assumption that a HS may be less attentive at specific environmental conditions (during the late evening or when the lighting is dim), rule-based classifier 410B may assign a low weight to respective measures features 30A, indicating that the reliability of the diagnosis of the HS as suffering from the suspected impediment under these environmental conditions may be low.

In another example, preprocessed test results 350 may include one or more features 30A pertaining to sensory input 230 that may have been measured during the HS's performance of personalized test 50A, and may correspond to a physical, emotional or mental condition of the HS (e.g., the HS's heart rate). Under the assumption that the test may be inaccurate when a HS is at such a condition (e.g., when the HS is excited), rule-based classifier 410B may assign a low weight to respective measures features 30A, indicating that the reliability of the diagnosis of the HS as suffering from the suspected impediment under these environmental conditions may be low.

As explained herein, at least one classifier 410B may be or may include a rule-based classification module. Additionally, or alternatively, at least one classification module 410B may be or may include an ML-based classification model, trained to receive one or more input data elements (e.g., a first data element or feature 30A extracted from preprocessed data elements 310, 320, 330, and/or 340; a second data element or feature 30A extracted from preprocessed test data input 350; a third data element of feature 30A pertaining to a profile data element; and an indication of the suspected impediment and/or atypical behavior 50B) and classify the HS according to one or more classes of developmental impediments.

According to some embodiments, specific classifier models 410B may be adapted to fine tune a classification of respective specific developmental impediments. For example, at least one classifier modules 410B may be associated with autism, and may be adapted to classify the HS, based on the input data to classes or groups, where each group represents a different manifestation or sub type of autism, as known in the art.

The one or more classification model 410B (e.g. a neural network) may be trained on a labeled training set of HSs to classify or categorize DCs of HSs according to classes of suspected developmental impediments, in a supervised training stage. The training stage may include a supervised learning process, as known in the art. For example, a classification model 410B may be trained by a human expert, who may diagnose HSs as suffering from one or more specific developmental impediments and label the HSs according to their diagnosis. The classification model 410B may thus be trained to receive data elements or features 30A pertaining to behavioral and/or DCs of additional HSs from beyond the training set, and classify the additional HSs as members of one or more groups that may be associated with one or more respective sub-classes of developmental impediments.

In some embodiments, analysis module 40' may provide a probability in which a user may be suffering from the suspected developmental impediment based on one or more of the preprocessed test results 350 and or preprocessed data elements 310, 320, 330, and 340. Analysis module 40' may receive (e.g., from input element 7 of FIG. 1) at least one distance metric (e.g., a Euclidean distance from a mean value of the class members) and calculate the value of the received metric for one or more HS represented in each classification model 410B, as known in the art. Analysis module 40' may subsequently produce an indication of the probability of the diagnosis as an inverse function of the calculated metric (e.g., as the metric value increases, the probability of diagnosis decreases).

In some embodiments of the present invention, analysis module 40' may produce a diagnosis indication 60A based on the predicted probability of the suspected developmental impediment. For example, if the predicted probability surpasses a first predefined threshold (e.g., 90%) then analysis module 40' may attribute diagnosis 60A as one of a high probability, and recommend a treatment 60B that may correspond with the diagnosis.

As explained herein analysis module 40' may provide, as part of diagnosis 60A an indication of one or more features 30A or data elements that may correspond to the suspected developmental impediment and/or atypical behavior. The indicated features 30A or data elements may be selected so as to support or negate a suspected developmental impediment.

For example, analysis module 40' may determine that the HS may be suffering from a specific developmental impediment (e.g., autism) and provide an indication of a specific behavioral feature 30A (e.g., a lack of eye-contact) that may be an outlier to typical EB 90A (e.g., maintaining eye-contact) as a supporting indication to the diagnosis. In another example, analysis module 40' may provide an indication of one or more specific data elements of feature 30A corresponding to a social condition (e.g., from structured input preprocessing NLP 321, indicating a lack of social connections) as a supporting indication to the diagnosis.

In a contrary example, at least one feature 30A may include an initial suspected diagnosis of a developmental impediment of the HS (e.g., from an MR 210, such as a historic diagnosis performed by a medical or healthcare practitioner). Analysis module 40' may determine that the HS may be not be suffering from the suspected, based on one for example or more sensory inputs 230 and/or the test outcome 250. Analysis module 40' may provide an indication of one or more specific data elements of feature 30A corresponding to the sensory inputs 230 and/or the test outcome 250 (e.g., indicating that the HS has maintained eye contact) to contradict or disprove the initial suspected diagnosis (e.g., of autism, Asperger syndrome, Down syndrome, intellectual disability, dyslexia, ADHD, brain injury, anxiety disorders, mental disability and the like).

Recommended treatment 60B may include, for example a referral to a specialist, for further care and treatment against the identified developmental impediment, alongside one or more of: diagnosis 60A, and a structured interface 60E that may be customized or standardized to provide information to a third-party entity, such as a physician, a social security authority, an insurance company and the like.

Additionally or alternatively, recommended treatment 60B may include one or more interactive activities that may be for example, exhibited or presented on a computing device of the HS. Such interactive activities may be stored for example on a treatment repository 81, and may include for example, games (e.g., game applications on computing devices, robots, virtual reality (VR) and/or augmented reality (AR) games, games on game consoles, online games, etc.) adapted to enhance social interaction, social skills, applications adapted to enhance forming eye contact, applications adapted to provide speech therapy, augmented and alternative communication (e.g. typing skills) video or music that may influence the HS (e.g., soothing videos and or music pieces), and the like.

Recommended treatment 60B may further correspond with or be dependent upon additional input data, such as data pertaining to MR 210, structured input 220, sensory input 230 and/or application input 240. The treatment may thus be personalized according to at least one input data element in addition to the test results outcome 250.

For example, in a case that the diagnosis is directed to a developmental condition of impaired social skills (e.g., as in Asperger's syndrome), a recommended treatment 60B may be directed to enhancing social skills. Such a treatment may include for example games (such as robot AR, VR games, application games, etc.) that may present visual and/or audible elements to the HS, and may be adapted to practice social skills such as maintaining eye contact, invoking empathy, exercising patience, exercising a vocabulary for friendly communication, etc.

In another example, in a case that the diagnosis is directed to a developmental condition of impaired motor skills, a recommended treatment 60B may be directed to enhancing motor skills. This may include for example games that may be adapted to improve characteristics of coarse and/or fine motor skills, gross motor movement, hand-eye coordination and manual dexterity (e.g., learning to type).

In some embodiments, one or more of diagnosis 60A and/or recommended treatment 60B may be presented by application 5 to the user on a UI (e.g., 70B) of a computing device, such as a smartphone, tablet or laptop.

In some embodiments, UI 70B may be implemented on the same computing device (e.g., a smartphone) as that of UI 70A. Additionally or alternatively, UI 70B may be implemented on a second computing device, different from that of UI 70A.

According to some embodiments, analysis module 40' may produce a recommend report or roadmap for treatment 60D based on at least one of the diagnosis of developmental condition and the one or more profile data elements. For example, a treatment roadmap 60D may include one or more recommended treatments 60B. The one or more treatment reports or roadmaps 60D may be stored e.g., on treatment repository 81. Treatment roadmap 60D may be associated with specific HS profiles, such that when given an HS's profile (e.g., age) and a respective diagnosis 60A, analysis module 40' may select one or more treatment roadmaps 60D to present (e.g., on UI 70B) to the HS and/or their parent or guardians. The presented roadmap may include for example: one or more recommended treatments 60B; duration and timing of the one or more recommended treatments 60B; and a prediction 60C of the expected developmental condition (e.g., showing the expected progress of the recommended treatment, if the treatment roadmap is adhered to).

Figure 6:
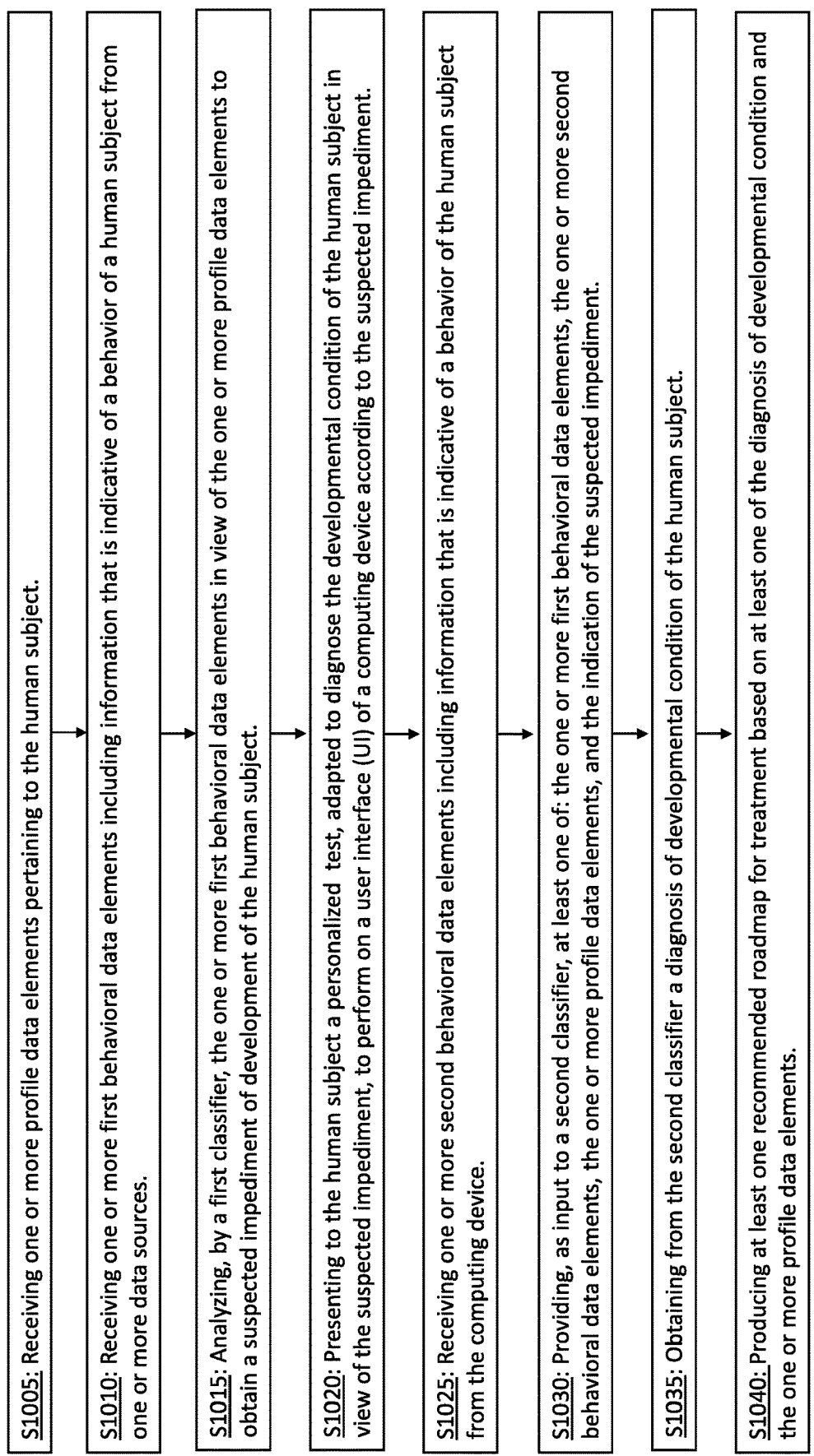
FIG. 6 is a flow diagram, depicting a method of diagnosing a developmental condition of the human subject, detecting a condition of impeded and producing a suggested roadmap for treatment development, according to some embodiments.

Reference is now made to FIG. 6, which is a flow diagram, depicting a method for diagnosing a DC of the HS, according to some embodiments.

As shown in step S1005, embodiments of the invention (e.g., element 10 of FIGS. 2 and/or 10' of FIG. 5) may receive one or more profile data elements (e.g., element 221 of FIG. 2) pertaining to the HS, including for example the HS's age, gender, geographic location.

As shown in step S1010, embodiments of the invention may receive one or more data elements or features (e.g., element(s) 30A of FIG. 2), such as one or more first behavioral data elements, including information that is indicative of a behavior of a human subject (e.g., a movement of the HS, an utterance of a sound and/or speech by the HS, a gaze of the HS and the like) from one or more data sources.

As shown in step S1015, embodiments of the invention may analyze (e.g., by a first classification module 410A of FIG. 2) the one or more first behavioral data elements and/or features 30A in view of the one or more profile data elements 221, to obtain a suspected impediment of development of the human subject.

Classification module 410A may classify an HS according to behavior and/or DC. For example, as explained herein, analysis module 40 may identify one or more discrepancies between an expected behavior (EB) and a monitored behavior (e.g., a behavioral feature 30A) and/or one or more discrepancies between an expected DC and a monitored DC (e.g., that may be included in a structured input 220 and extracted by preprocessing module 30 as a feature 30A). Classification module 410A may subsequently classify an HS according to the identified discrepancies, in view of the HS profile (e.g., their age) to determine a suspected developmental impediment 50B.

As shown in step S1020, embodiments of the invention may present to the HS a personalized test, adapted to diagnose the developmental condition of the human subject in view of the suspected impediment, to perform on a UI of a computing device (e.g., UI 70A) according to the suspected impediment. For example, as elaborated herein, embodiments of system 10 may include a test repository 80 that may include one or more test templates, each corresponding to at least one respective suspected developmental impediment 50B. Analysis module 40 may select a template corresponding to the suspected developmental impediment 50B, and adapt the test to be tailored or personalized according to at least one of the HS profile parameters (e.g., age, gender, spoken language, etc.), and present the adapted test on a UI (e.g., on the HS's smartphone).

As shown in step S1025, following presentation of the test, embodiments of the invention may receive (e.g., from an application 5 that may be executed on the HS's computing device) one or more second behavioral data elements (e.g., test results 250 of FIG. 5). The one or more second behavioral data elements may include information that is indicative of a behavior of the human subject from the computing device. For example, the test may be presented by a non-spontaneous, interactive application, that may be configured to monitor at least one data element pertaining to the HS's behavior (e.g., a movement, a facial expression and the like), and provide the monitored data as input to an embodiment of the invention (e.g., element 10 of FIGS. 2 and/or 10' of FIG. 5).

As shown in step S1030, embodiments of the invention may provide, as input to a second classifier (e.g., 410B of FIG. 5), at least one of: the one or more first behavioral data elements, the one or more second behavioral data elements, the one or more profile data elements, and the indication of the suspected impediment 50B.

As shown in step S1035, embodiments of the invention may obtain, from the second classifier 410B, a diagnosis 60A of developmental condition of the HS. According to some embodiments, as explained herein, second classifier 410B may be implemented as a rule-based classifier adapted to ascertain whether the HS may be suffering from the suspected developmental impediment 50B in a high level of certainty. Additionally, or alternatively, as elaborated herein, second classifier 410B may be implemented as any type of neural network, ML-based classifier, adapted to fine-tune the suspected impediment 50B to subclasses and/or types or severities of the developmental impediment.

As shown in FIG. 5, embodiments may include a treatment repository (e.g., element 81 of FIG. 5). The treatment repository 60D may include recommended treatments that may correspond to diagnosed developmental impediments, and may be designed by diagnostic and/or treatment specialists.

As shown in step S1040, embodiments of the invention may select one or more recommended roadmaps for treatment 60D (e.g., from treatment repository 81 of FIG. 5), based on or corresponding with at least one of the diagnosis 60A of developmental condition and the one or more profile data elements 221 (e.g., the HS's age and gender). The roadmap for treatment 60D may include, for example a listing or description of one or more treatments, exercises and/or tests that may be performed by the HS over a predefined period of time, or predefined points in time so as to improve their condition in view of the diagnosed DC and/or developmental impediment.

As explained herein, the present invention may include a practical application for automatically producing a personalized screening test, for detecting a developmental impediment of a human subject, assessing the human subject's developmental condition, and producing a roadmap for treatment, in view of expected progress in development.

As explained herein, currently available methods for diagnosis and treatment of a human subject's developmental condition may include obstacles for disabled people and their families. Diagnostic and therapeutic know-how that may be accumulated and developed by a plurality of physicians, clinicians, care givers and therapists may be practically inaccessible to a wide portion of the human population leaving crucial professional knowledge, research, best practices and intellectual capital in the field of disabilities laying within organizations, academia and professionals as local silos reaching few. Efficient crossroads to reach consumers and correctly disseminate and implement are acutely needed to reduce current fragmentation of diagnosis and treatment.

Embodiments of the invention may effectively improve the health and quality of life of millions in need around the globe by enhancing acute early diagnosis alongside individualized targeted treatment, making sure each user will have the best tools to reach their maximum potential thus enhancing quality of life, social and medical systems, making sure no one in need is left behind.

Embodiments of the present invention may include a practical application for disseminating this diagnostic and therapeutic know-how, and thus facilitating a screening test to identify human subjects that may require treatment, and allowing treatment to these identified people.

Harnessing the power of big-data processing and analysis, embodiments of the invention may include an improvement over currently available screening diagnostic technologies by facilitating diagnosis of human developmental conditions based on aggregation of data pertaining to different sources and formats, such as historical MR, structured input and sensory input, to obtain a diagnosis that may be based on real-time or near real time combination of the aggregated data.

Moreover, embodiments of the present invention may include an improvement over currently available screening diagnostic technologies by applying a hierarchical, iterative diagnosis scheme, starting from a general screening test, and fine-tuning the diagnosis through an iterative process of classification. Each classification module may be adapted to fine-tune the classification of the suspected developmental impediments to sub classes and/or severities of the HS's DC. Each classification module may be specifically adapted to determine, in a high level of probability, whether the HS indeed suffers from the diagnosed DC.

Another aspect of improvement over currently available diagnostic technologies may include the personalization and/or tailoring the process of diagnosis to the specific HS (e.g., parameters of their profile), and/or to the environmental conditions surrounding the HS (e.g., environmental conditions).

Another aspect of improvement over currently available diagnostic technologies may include the personalization of a roadmap for treatment based on at least one of the diagnosis of developmental condition and the one or more profile data elements, to facilitate following-up on the advancement of treatment per the specific HS.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention. Further, features or elements of different embodiments may be used with or combined with other embodiments.

The invention claimed is:

1. A method of performing screening tests for diagnosing a developmental condition of a human subject, by at least one processor, the method comprising:
    receiving one or more profile data elements pertaining to the human subject;
    receiving one or more first behavioral data elements comprising information that is indicative of a behavior of a human subject from one or more data sources;
    analyzing the one or more first behavioral data elements in view of the one or more profile data elements, to obtain a suspected impediment of development of the human subject; and
    presenting to the human subject a personalized test, adapted to diagnose the developmental condition of the human subject in view of the suspected impediment, to perform on a user interface (UI) of a computing device, according to the suspected impediment, wherein the personalized test is presented by an application on the UI of the computing device, and wherein the application is selected from a list comprising:
    a spontaneous, interactive application;
    a spontaneous, non-interactive application; and
    a non-spontaneous, interactive application.

2. The method of claim 1, wherein analyzing the one or more first behavioral data elements comprises:
    providing at least one of the one or more first behavioral data elements and the one or more profile data elements as input to a first classifier;
    obtaining from the first classifier an indication of the suspected impediment of development of the human subject.

3. The method of claim 1, wherein the test is personalized according to at least one of:
    a profile data element;
    a data element corresponding to an environmental condition at the human subject's environment;
    a data element corresponding to a physical condition of the human subject;
    a data element corresponding to a medical record of the human subject; and
    a data element corresponding to a structured input of the human subject.

4. The method of claim 1, wherein presenting the personalized test to perform on the UI comprises:
    receiving one or more second behavioral data elements comprising information that is indicative of a behavior of the human subject from the computing device;
    providing, as input to a second classifier, at least one of: the one or more first behavioral data elements, the one or more second behavioral data elements, the one or more profile data elements, and the indication of the suspected impediment; and
    obtaining from the second classifier a diagnosis of developmental condition of the human subject.

5. The method of claim 1, wherein the diagnosis of developmental condition comprises one or more of:
    the suspected impediment;
    a developmental condition classification of the human subject corresponding to suspected impediment;
    a level of diagnosis certainty; and
    an indication of one or more behavioral data elements that correspond to the suspected developmental impediment.

6. The method of claim 1, further comprising producing at least one recommended roadmap for treatment based on at least one of the diagnosis of developmental condition and the one or more profile data elements.

7. The method of claim 1, further comprising producing at least one of:
    a predicted roadmap of a developmental condition of the human subject; and
    a predicted roadmap of behavior of the human subject,
based on at least one of the diagnosis of developmental condition and the one or more profile data elements.

8. The method of claim 1, wherein the one or more data sources are selected from a list consisting of:
    a structured text document;
    a medical database; and
    at least one sensor adapted to sense a physical property indicative of a behavior of the human subject.

9. The method of claim 1, wherein the sensor is a wearable sensor, adapted to sense at least one physical property and wherein the physical property is selected from a list comprising one or more of: skin temperature, skin moisture, skin pH, skin conductivity, pulse rate, blood pressure, movement, acceleration, firmness of touch, brain wave signals, eye gaze, and a spectral distribution of skin color.

10. The method of claim 1, wherein the sensor is comprised within a computing device, adapted to execute at least one application, and wherein the application is adapted to obtain from the sensor at least one behavioral data element comprising information that is indicative of a behavior of the human subject.

11. The method of claim 1, wherein at least one behavioral data element is a voice of the human and wherein the application is configured to record a voice of the human subject during presentation of the application on the UI and analyze the recorded voice to obtain a value of at least one acoustic parameter that is indicative of a behavior of the human subject.

12. The method of claim 1, wherein at least one behavioral data element is a voice of the human subject, and wherein the application is configured to record the voice of the human subject during a normal operation of the computing device by the human subject and analyze the recorded voice to obtain a value of at least one acoustic parameter that is indicative of a behavior of the human subject.

13. The method of claim 1, wherein at least one behavioral data element is a picture of the human subject and wherein the application is configured to take at least one picture of the human subject during presentation of the application on the UI and analyze the at least one picture to obtain a value of at least one visual parameter that is indicative of a behavior of the human subject.

14. The method of claim 1, wherein at least one behavioral data element is a picture of the human subject and wherein the application is configured to take at least one picture of the human subject during a normal operation of the computing device by the human subject and analyze the at least one picture to obtain at least one visual parameter that is indicative of at least one of a behavior of the human subject.

15. The method of claim 1, wherein at least one behavioral data element is a movement of the human subject, and wherein the application is configured to monitor at least one movement of the human subject during presentation of the application on the UI and analyze the at least one movement to obtain a value of at least one movement parameter that is indicative of a behavior of the human subject.

16. The method of claim 1, wherein at least one behavioral data element is a movement of the human subject and wherein the application is configured to monitor at least one movement of the human subject during a normal operation of the computing device by the human subject and analyze the at least one movement to obtain a value of at least one movement parameter that is indicative of a behavior of the human subject.

17. A system for performing screening tests for diagnosing a developmental condition of a human subject, the system comprising: a non-transitory memory device, wherein modules of instruction code are stored, and at least one processor associated with the memory device, and configured to execute the modules of instruction code, whereupon execution of said modules of instruction code, the at least one processor is configured to:

receive one or more profile data elements pertaining to the human subject;
receive one or more first behavioral data elements comprising information that is indicative of a behavior of a human subject from one or more data sources;
analyze the one or more first behavioral data elements in view of the one or more profile data elements to obtain a suspected impediment of development of the human subject; and
present to the human subject a personalized test, adapted to diagnose the developmental condition of the human subject in view of the suspected impediment, to perform on a user interface (UI) of a computing device according to the suspected impediment, wherein the personalized test is presented by an application on the UI of the computing device, and wherein the application is selected from a list comprising:
a spontaneous, interactive application;
a spontaneous, non-interactive application; and
a non-spontaneous, interactive application.

18. A method of performing screening tests for diagnosing a developmental condition of a human subject by at least one processor, the method comprising:
obtaining one or more behavioral data elements, comprising information that is indicative of a behavior of a human subject, during spontaneous, non-interactive utilization of a smart device;
analyzing the one or more behavioral data elements to obtain a suspected impediment of development of the human subject; and
presenting to the human subject, on a UI, a personalized test, adapted to diagnose the developmental condition of the human subject in view of the suspected impediment.

* * * * *